US012691151B2

(12) United States Patent
McFadden et al.

(10) Patent No.: US 12,691,151 B2
(45) Date of Patent: *Jul. 28, 2026

(54) METHODS AND COMPOSITIONS FOR IMPROVING ONCOLYTIC VIRUS INFECTION FOR NONPERMISSIVE CANCERS

(71) Applicant: Arizona Board of Regents on behalf of Arizona State University, Scottsdale, AZ (US)

(72) Inventors: Douglas Grant McFadden, Tempe, AZ (US); Mohammed Masmudur Rahman, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1185 days.

This patent is subject to a terminal disclaimer.

(21) Appl. No.: 17/639,563

(22) PCT Filed: Sep. 1, 2020

(86) PCT No.: PCT/US2020/048932
§ 371 (c)(1),
(2) Date: Mar. 1, 2022

(87) PCT Pub. No.: WO2021/046048
PCT Pub. Date: Mar. 11, 2021

(65) Prior Publication Data
US 2022/0296660 A1 Sep. 22, 2022

Related U.S. Application Data

(60) Provisional application No. 62/913,667, filed on Oct. 10, 2019, provisional application No. 62/894,929, filed on Sep. 2, 2019.

(51) Int. Cl.
*A61K 35/768* (2015.01)
*A61K 31/366* (2006.01)
*A61K 31/497* (2006.01)
*A61P 35/00* (2006.01)

(52) U.S. Cl.
CPC .......... *A61K 35/768* (2013.01); *A61K 31/366* (2013.01); *A61K 31/497* (2013.01); *A61P 35/00* (2018.01)

(58) Field of Classification Search
None
See application file for complete search history.

(56) References Cited

U.S. PATENT DOCUMENTS

| | | |
|---|---|---|
| 10,238,700 B2 | 3/2019 | Szalay et al. |
| 2004/0014034 A1 | 1/2004 | Evans et al. |
| 2009/0035276 A1 | 2/2009 | McFadden et al. |
| 2012/0100109 A1 | 4/2012 | Zhang et al. |
| 2014/0134134 A1* | 5/2014 | Mcfadden ............... A61P 35/00 |
| | | 435/235.1 |
| 2021/0301263 A1 | 9/2021 | McFadden et al. |

FOREIGN PATENT DOCUMENTS

| | | |
|---|---|---|
| WO | WO-2004015118 A1 | 2/2004 |
| WO | WO-2004022729 A1 | 3/2004 |
| WO | WO-2020033510 A1 | 2/2020 |
| WO | WO-2021046048 A1 | 3/2021 |

OTHER PUBLICATIONS

Bachmann et al., J Biol Chem., Mar. 17, 2006, 281(11):7357-63. (Year: 2006).*
Bachmann et al., A nuclear transport signal in mammalian target of rapamycin is critical for its cytoplasmic signaling to S6 kinase 1. J Biol Chem 281(11):7357-7363 (2006).
Cameron et al. The complete DNA sequence of Myxoma Virus. Virology 264:298-318 (1999).
Chan et al., Oncolytic Myxoma Virus: The path to clinic. Vaccine 31(39):4252-4258 (2013).
Chan et al., Oncolytic Poxviruses. Annu Rev Virol 1(1):119-141 (2014).
Chan et al. Oncolytic poxviruses. Annual review of virology 1:191-214 (2014).
Dickmanns et al. Structural Basis of Targeting the Exportin CRM1 in Cancer. Cells 4(3):538-68 (2015).
Hou, J. Interactions of Vaccinia virus with the host cell. [2016 Thesis] The University of Edinburgh; https://www.era.lib.ed.ac.uk/handle/1842/22898?show=full (pub. 2017).
Kalesse et al. The chemistry and biology of ratjadone. Chembiochem. 2(9):709-14 (2001).
Koster et al. Ratjadones inhibit nuclear export by blocking CRM1/exportin 1. Exp Cell Res, 286(2):321-31 (2003).
Kudo et al. Leptomycin B inhibition of signal-mediated nuclear export by direct binding to CRAII. Exp Cell Res 242(2):540-7 (1998).
Lichty et al. Going viral with cancer immunotherapy. Nature Reviews Cancer 14:559-567 (2014).
Mathew et al. CRM1 inhibitors for antiviral therapy. Frontiers in Microbiology 8:1171 (2017).
McFadden. Poxvirus tropism. Nat Rev Microbiol 3(3):201-13 (2005).

(Continued)

*Primary Examiner* — Nicole Kinsey White
(74) *Attorney, Agent, or Firm* — Riverside Law LLP

(57) ABSTRACT

Disclosed herein are methods and compositions of treating cancer, comprising administrating to a subject with cancer a therapeutically effective amount of an oncolytic virus and a nucleocytoplasmic transport inhibitor. Further described herein are methods of converting a nonpermissive cancer cell to a permissive cancer cell and methods of killing a cancer cell by contacting the cancer cell with a therapeutically effective amount of an oncolytic vims and a nucleocytoplasmic transport inhibitor.

7 Claims, 6 Drawing Sheets

(56) References Cited

OTHER PUBLICATIONS

Moss. Chapter 84: Poxviridae: The Viruses and Their Replication. Fields' virology B. N. Fields, D. M. Knipe, p. M. Howley, D. E. Griffin, Eds. (Lippincott Williams & Wilkins, Philadelphia (pp. 2849-2883) (2001).

Mutka et al. Identification of nuclear export inhibitors with potent anticancer activity in vivo. Cancer Res. 69(2):510-7 (2009).

Oh et al., Host cell nuclear proteins are recruited to cytoplasmic vaccinia virus replication complexes. Journal of Virology 79(20):12852-12860 (2005).

PCT/US2019/045452 International Search Report and Written Opinion dated Nov. 8, 2019.

PCT/US2020/048932 International Search Report and Written Opinion dated Dec. 9, 2020.

Pemberton et al. Paschal, Mechanisms of receptor-mediated nuclear import and nuclear export. Traffic 6(3):187-98 (2005).

Postigo et al. Cytoplasmic ATR Activation Promotes Vaccinia Virus Genome Replication. Cell Rep 19(5):1022-1032 (2017).

Rahman et al. Identification of host DEAD-box RNA helicases that regulate cellular tropism of oncolytic Myxoma virus in human cancer cells. Sci Rep 7(1):15710 (2017).

Realegeno et al. Monkeypox Virus Host Factor Screen Using Haploid Cells Identifies Essential Role of GARP Complex in Extracellular Virus Formation. J Virol 91(11):e00011-17 (2017).

Seet et al. Poxviruses and immune evasion. Annu Rev Immunol 21:377-423 (2003).

Smith et al. Vaccinia virus immune evasion: mechanisms, virulence and immunogenicity. J Gen Virol 94(Pt 11):2367-92 (2013).

Turner et al. Nuclear export of proteins and drug resistance in cancer. Biochem Pharmacol 83(8):1021-32 (2012).

Upton et al. Poxvirus orthologous clusters: toward defining the minimum essential poxvirus genome. J Virol 77(13):7590-600 (2003).

Adam et al. Synergistic and Selective Cancer Cell Killing Mediated by the Oncolytic Adenoviral Mutant AdΔΔ and Dietary Phytochemicals in Prostate Cancer Models. Hum Gene Ther 23(9):1003-1015 (2012).

Fehl et al. Curcumin promotes the oncoltyic capacity of vesicular stomatitis virus for the treatment of prostate cancers. Virus Res 228:14-23 (2017).

Riaz et al. Selinexor. Exportin-1 (XPO1) inhibitor, Oncolytic. Drugs of the Future 39(10):685 (2014).

Zemp et al. Treating brain tumor-initiating cells using a combination of myxoma virus and rapamycin. Neuro Oncol 15(7):904-920 (2013).

EP Application No. 19846898.5 Extended European Search Report dated Apr. 11, 2022.

Fahy et al.: Vaccinia virus protein C16 acts intracellularly to modulate the host response and promote virulence. J Gen Virol. 89(Pt 10):2377-2387 doi:10.1099/vir.0.2008/004895-0 (2008).

Lundberg et al.: Selective Inhibitor of Nuclear Export (SINE) Compounds Alter New World Alphavirus Capsid Localization and Reduce Viral Replication in Mammalian Cells. PLoS Negl Trop Dis. 10(11):e0005122:1-24 doi:10.1371/journal.pntd.0005122 (2016).

Sun et al.: Inhibiting cancer cell hallmark features through nuclear export inhibition. Signal Transduct Target Ther. 1:16010:1-10 doi: 10.1038/sigtrans.2016.10 (2016).

* cited by examiner

METHODS AND COMPOSITIONS FOR IMPROVING ONCOLYTIC VIRUS INFECTION FOR NONPERMISSIVE CANCERS

CROSS-REFERENCE TO RELATED APPLICATIONS

This application is a U.S. national phase application filed under 35 U.S.C. § 371 claiming benefit to International Patent Application No. PCT/US2020/048932, filed Sep. 1, 2020, which claims priority to U.S. Provisional Patent Application No. 62/913,667, filed Oct. 10, 2019, and U.S. Provisional Patent Application No. 62/894,929, filed Sep. 2, 2019, the disclosures of each of which are incorporated herein by reference in their entireties.

STATEMENT OF GOVERNMENT SUPPORT

This invention was made with government support under grant number R01 A1080607 awarded by the National Institutes of Health. The government has certain rights in the invention.

TECHNICAL FIELD

This disclosure relates to oncolytic virus and, in particular, the use of oncolytic virus in combination with a nucleocytoplasmic transport inhibitor.

BACKGROUND

Oncolytic viruses, such as from t he Poxviridae family of viruses, are mammalian viruses that are designed and/or selected for their ability to selectively infect and kill transformed cancer cells, and by their ability to activate host's immune system against not only the virus, but also tumor antigens (see for example, Lichty B D, Breitbach C J, Stojdl D F, Bell J C. 2014. *Going viral with cancer immunotherapy.* Nature Reviews Cancer 14:559-567). However, the application of oncolytic viruses can be limited in certain tumor cells, for example nonpermissive tumor cells. Therefore, there remains a need to improve therapies based on oncolytic viruses.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Disclosed herein, in some aspects, is a method of treating cancer, comprising administering to a subject a therapeutically effective amount of an oncolytic virus, and a nucleocytoplasmic transport inhibitor.

In some embodiments, the oncolytic virus is derived from the Poxviridae family. In some embodiments, the oncolytic virus is derived from Chordopoxvirinae subfamily or Entomopoxvirinae subfamily. In some embodiments, the oncolytic virus is derived from a virus genus of *Orthopoxvirus, Cervidpoxvirus, Parapoxvirus, Avipoxvirus, Capripoxvirus, Leporipoxvirus, Suipoxvirus, Molluscipoxvirus, Yatapoxvirus, Alphaentomopoxvirus, Betaentomopoxvirus,* or *Gam-*

*maentopoxvirus.* In some embodiments, the oncolytic virus is derived from genus *Leporipoxvirus.* In some embodiments, the oncolytic virus is a myxoma virus (MYXV). In some embodiments, the oncolytic virus is derived from genus *Orthopoxvirus.* In some embodiments, the virus is genetically modified. In some embodiments, the nucleocytoplasmic transport inhibitor is selected from the group consisting of Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor. In some embodiments, the nucleocytoplasmic transport inhibitor is Leptomycin B. In some embodiments, the nucleocytoplasmic transport inhibitor is Selinexor. In some embodiments, the cancer is a solid tumor. In some embodiments, the solid tumor is a sarcoma or a carcinoma. In some embodiments, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, or retinoblastoma. In some embodiments, the solid tumor is colorectal adenocarcinoma, pancreatic cancer, or melanoma. In some embodiments, the oncolytic virus and the nucleocytoplasmic transport inhibitor are administered simultaneously. In some embodiments, the oncolytic virus and the nucleocytoplasmic transport inhibitor are administered sequentially. In some embodiments, the oncolytic virus is administered before administering the nucleocytoplasmic transport inhibitor. In some embodiments, the oncolytic virus is administered after administering the nucleocytoplasmic transport inhibitor. In some embodiments, the method comprises administering the oncolytic virus and the nucleocytoplasmic transport inhibitor for a period of at least 1 day, at least 2 days, at least 3 days, at least 1 week, at least 2 weeks, at least 3 weeks, at least 4 weeks, at least 1 month, at least 3 months, at least 6 months, or at least 1 year. In some embodiments, the method comprises administering the oncolytic virus, the nucleocytoplasmic transport inhibitor, or both to the subject twice a week, once a week, once every two weeks, once every three weeks, once every four weeks, once a month, or once every two months. In some embodiments, the oncolytic virus is administered locally to a cancer tissue to be treated. In some embodiments, the oncolytic virus is administered by intratumoral injection. In some embodiments, a multiplicity of infection (MOI) of the oncolytic virus for the tissue is from about 0.01 to about 10. In some embodiments, a multiplicity of infection (MOI) of the oncolytic virus for the tissue is from about 0.05 to about 5. In some embodiments, a concentration of the nucleocytoplasmic transport inhibitor at the tissue is from about 0.0001 µM to about 100 µM. In some embodiments, a concentration of the nucleocytoplasmic transport inhibitor at the tissue is from about 0.01 μM to about 1 μM.

Disclosed herein, in some aspects, is a method of killing a cancer cell comprising: contacting the cancer cell with an oncolytic virus and a nucleocytoplasmic transport inhibitor, thereby killing the cancer cell.

Disclosed herein, in some aspects, is a method of enhancing susceptibility of a cancer cell to infection by an oncolytic virus, comprising contacting the cancer cell to an oncolytic virus and a nucleocytoplasmic transport inhibitor.

Disclosed herein, in some aspects, is a method of inducing a cancer cell to be susceptible to infection by an oncolytic virus, comprising contacting the cancer cell to the oncolytic virus and a nucleocytoplasmic transport inhibitor.

Disclosed herein, in some aspects, is a method of converting a nonpermissive cancer cell to a permissive cancer cell comprising contacting the nonpermissive cancer cell with an oncolytic virus and a nucleocytoplasmic transport inhibitor.

Disclosed herein, in some aspects, is a method of increasing proliferation of an oncolytic virus in a cancer cell that is not susceptible to infection by the oncolytic virus comprising contacting the cancer cell to an oncolytic virus and a nucleocytoplasmic transport inhibitor.

In some embodiments, the oncolytic virus is a virus from the Poxviridae family. In some embodiments, the oncolytic virus is a virus from Chordopoxvirinae subfamily or Entomopoxvirinae subfamily. In some embodiments, the oncolytic virus is from a virus genus that is *Orthopoxvirus*, *Cervidpoxvirus*, *Parapoxvirus*, *Avipoxvirus*, *Capripoxvirus*, *Leporipoxvirus*, *Suipoxvirus*, *Molluscipoxvirus*, *Yatapoxvirus*, *Alphaentomopoxvirus*, *Betaentomopoxvirus*, or *Gammaentomopoxvirus*. In some embodiments, the oncolytic virus is from genus *Leporipoxvirus*. In some embodiments, the oncolytic virus is a myxoma virus (MYXV). In some embodiments, the oncolytic virus is from genus *Orthopoxvirus*. In some embodiments, the virus is genetically modified. In some embodiments, the nucleocytoplasmic transport inhibitor is selected from the group consisting of Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor. In some embodiments, the nucleocytoplasmic transport inhibitor is Leptomycin B. In some embodiments, the nucleocytoplasmic transport inhibitor is Selinexor. In some embodiments, the cancer cell is colorectal cancer cell, pancreatic cancer cell, melanoma cancer cell. In some embodiments, the cancer cell is a human cancer cell. In some embodiments, the cancer cell is contacted to an oncolytic virus and a nucleocytoplasmic transport inhibitor in vivo. In some embodiments, the cancer cell is contacted to an oncolytic virus and a nucleocytoplasmic transport inhibitor ex vivo. In some embodiments, the method comprises contacting the cancer cell with the oncolytic virus and the nucleocytoplasmic transport inhibitor simultaneously. In some embodiments, the method comprises contacting the cancer cell with the oncolytic virus and the nucleocytoplasmic transport inhibitor sequentially. In some embodiments, the cancer cell is contacted with the oncolytic virus before being contacted with the nucleocytoplasmic transport inhibitor. In some embodiments, the cancer cell is contacted with the nucleocytoplasmic transport inhibitor before being contacted with the oncolytic virus. In some embodiments, the cancer cell is contacted with the oncolytic virus at a MOI of from about 0.01 to about 10. In some embodiments, the cancer cell is contacted with the oncolytic virus at a MOI of from about 0.05 to about 5. In some embodiments, the method comprises incubating the cancer cell in a media comprising the nucleocytoplasmic transport inhibitor at a concentration of from about 0.0001 μM to about 100 μM. In some embodiments, the method comprises incubating the cancer cell in a media comprising the nucleocytoplasmic transport inhibitor at a concentration of from about 0.01 μM to about 1 μM. In some embodiments, the method comprises contacting the cancer cell with a media comprising the nucleocytoplasmic transport inhibitor at a concentration of from about 0.0001 μM to about 100 μM. In some embodiments, the method comprises contacting the cancer cell with a media comprising the nucleocytoplasmic transport inhibitor at a concentration of from about 0.01 μM to about 1 μM. In some embodiments, the method further comprises contacting the oncolytic virus to an autologous or heterologous cell ex vivo. In some embodiments, the autologous or heterologous cell is a bone marrow cell or a macrophage cell. In some embodiments, the method further comprises injecting the autologous or heterologous cell to the subject.

Disclosed herein, in some aspects is a pharmaceutical composition comprising: an oncolytic virus, and a nucleocytoplasmic transport inhibitor.

In some embodiments, the pharmaceutical composition further comprises a pharmaceutically acceptable excipient or carrier. In some embodiments, the oncolytic virus is derived from the Poxviridae family. In some embodiments, the oncolytic virus is derived from Chordopoxvirinae subfamily or Entomopoxvirinae subfamily. In some embodiments, the oncolytic virus is derived from a virus genus of *Orthopoxvirus*, *Cervidpoxvirus*, *Parapoxvirus*, *Avipoxvirus*, *Capripoxvirus*, *Leporipoxvirus*, *Suipoxvirus*, *Molluscipoxvirus*, *Yatapoxvirus*, *Alphaentomopoxvirus*, *Betaentomopoxvirus*, or *Gammaentomopoxvirus*. In some embodiments, the oncolytic virus is derived from genus *Leporipoxvirus*. In some embodiments, the oncolytic virus is a myxoma virus (MYXV). In some embodiments, the oncolytic virus is derived from genus *Orthopoxvirus*. In some embodiments, the virus is genetically modified. In some embodiments, the nucleocytoplasmic transport inhibitor is selected from the group consisting of Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor. In some embodiments, the nucleocytoplasmic transport inhibitor is Leptomycin B. In some embodiments, the nucleocytoplasmic transport inhibitor is Selinexor. In some embodiments, the pharmaceutical composition is in a unit dosage form suitable for intratumoral or parenteral administration. In some embodiments, the unit dosage comprises from about $1 \times 10^3$ plaque-forming units (PFU) to about $1 \times 10^{10}$ PFU of the oncolytic virus per mL. In some embodiments, the unit dosage comprises from about $1 \times 10^5$ PFU to about $1 \times 10^{10}$ PFU of the oncolytic virus per mL. In some embodiments, a weight ratio between the oncolytic virus and the nucleocytoplasmic transport inhibitor is from about $1 \times 10^9$ to about $1 \times 10^{-9}$.

Some embodiments relate to a method of treating cancer, comprising administering to a subject a therapeutically effective amount of an oncolytic virus, and a nucleocytoplasmic transport inhibitor. In one aspect, described herein is a method of killing a cancer cell comprising: contacting a cancer cell with a therapeutically effective amount of an oncolytic virus and a nucleocytoplasmic transport inhibitor, thereby killing said cancer cell. In one aspect, described herein is a method of enhancing susceptibility of a cancer cell to infection by an oncolytic virus, comprising: contacting the cancer cell to an oncolytic virus and a nucleocytoplasmic transport inhibitor. In one aspect, described herein is a method of making a cancer cell susceptible to infection by an oncolytic virus, comprising contacting the cancer cell to the oncolytic virus and a nucleocytoplasmic transport inhibitor. In one aspect, described herein is a method of converting a nonpermissive cancer cell to a permissive cancer cell comprising: contacting the nonpermissive cancer cell to an oncolytic virus to a therapeutically effective amount of said oncolytic virus and a nucleocytoplasmic transport inhibitor. In one aspect, described herein is a method of increasing proliferation of an oncolytic virus in a cancer cell that is not susceptible to infection by the oncolytic virus, comprising: contacting the cancer cell to an oncolytic virus and a nucleocytoplasmic transport inhibitor. In some embodiments, the oncolytic virus is a virus from the Poxviridae family. In some embodiments, the oncolytic virus is a virus from Chordopoxvirinae subfamily or Entomopoxvirinae subfamily. In some embodiments, the oncolytic virus is from a virus genus that is *Orthopoxvirus, Cervidpoxvirus, Parapoxvirus, Avipoxvirus, Capripoxvirus, Leporipoxvirus, Suipoxvirus, Molluscipoxvirus, Yatapoxvirus, Alphaentomopoxvirus, Betaentomopoxvirus,* or *Gammaentomopoxvirus.* In some embodiments, the oncolytic virus is from genus *Leporipoxvirus.* In some embodiments, the oncolytic virus is a myxoma virus (MYXV). In some embodiments, the oncolytic virus is from genus *Orthopoxvirus.* In some embodiments, the virus is genetically modified. In some embodiments, the nucleocytoplasmic transport inhibitor is selected from the group consisting of Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor. In some embodiments, the nucleocytoplasmic transport inhibitor is Leptomycin B. In some embodiments, the nucleocytoplasmic transport inhibitor is Selinexor. In some embodiments, the cell is a Human A549 cell, a HeLa cell, a 239 cell, or a primate Vero cell. In some embodiments, the cell is a human cell. In some embodiments, the cell is an in vivo cell, an in vitro cell, or an ex vivo cell. In some embodiments, the cancer is a solid tumor. In some embodiments, the solid tumor is a sarcoma or a carcinoma. In some embodiments, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, or retinoblastoma. In some embodiments, the solid tumor is colorectal adenocarcinoma, pancreatic cancer, or melanoma. In some embodiments, the oncolytic virus and said nucleocytoplasmic transport inhibitor are administered simultaneously or sequentially. In some embodiments, the oncolytic virus is administered before administering said nucleocytoplasmic transport inhibitor. In some embodiments, the oncolytic virus is administered after administering said nucleocytoplasmic transport inhibitor. In some embodiments, the method comprises administering said oncolytic virus and said nucleocytoplasmic transport inhibitor for a period of at least 1 day, at least 2 days, at least 3 days, at least 1 week, at least 2 weeks, at least 3 weeks, at least 4 weeks, at least 1 month, at least 3 months, at least 6 months, or at least 1 year. In some embodiments, the method comprises administering said oncolytic virus, said nucleocytoplasmic transport inhibitor, or both to said subject twice a week, once a week, once every two weeks, once every three weeks, once every four weeks, once a month, or once every two months. In some embodiments, the oncolytic virus is administered locally to a cancer tissue to be treated. In some embodiments, the oncolytic virus is administered by injection. In some embodiments, a multiplicity of infection (MOI) of said oncolytic virus for said tissue is from about 0.01 to about 10. In some embodiments, a multiplicity of infection (MOI) of said oncolytic virus for said tissue is from about 0.05 to about 5. In some embodiments, a concentration of said nucleocytoplasmic transport inhibitor at said tissue is from about 0.0001 µM to about 100 µM. In some embodiments, a concentration of said nucleocytoplasmic transport inhibitor at said tissue is from about 0.01 µM to about 1 µM. In some embodiments, the method comprises contacting said cancer cell with said oncolytic virus and said nucleocytoplasmic transport inhibitor simultaneously or sequentially. In some embodiments, the cancer cell is contacted with said oncolytic virus before with said nucleocytoplasmic transport inhibitor. In some embodiments, the cancer cell is contacted with said nucleocytoplasmic transport inhibitor before with said oncolytic virus. In some embodiments, the method comprises pre-treating said cancer cell with said nucleocytoplasmic transport inhibitor before said cancer cell is contacted with said oncolytic virus. In some embodiments, the cancer cell is contacted with said oncolytic virus at an MOI of from about 0.01 to about 10. In some embodiments, the cancer cell is contacted with said oncolytic virus at an MOI of from about 0.05 to about 5. In some embodiments, the method comprises incubating said cancer cell in a media comprising said nucleocytoplasmic transport inhibitor at a concentration of from about 0.0001 µM to about 100 µM. In some embodiments, the method comprises incubating said cancer cell in a media comprising said nucleocytoplasmic transport inhibitor at a concentration of from about 0.01 µM to about 1 µM. In some embodiments, the method comprises contacting said cancer cell with a media comprising said nucleocytoplasmic transport inhibitor at a concentration of from about 0.0001 µM to about 100 µM. In some embodiments, the method comprises contacting said cancer cell with a media comprising said nucleocytoplasmic transport inhibitor at a concentration of from about 0.01 µM to about 1 µM. In some embodiments, the method comprises contacting said oncolytic virus to an autologous or heterologous cell ex vivo. In some embodiments, the autologous or heterologous cell is a bone marrow cell or a macrophage cell. In some embodiments, the method comprises injecting said autologous or heterologous cell into said subject.

In one aspect, described herein is a pharmaceutical composition comprising: an oncolytic virus, and a nucleocytoplasmic transport inhibitor. In some embodiments, the pharmaceutical composition further comprises a pharmaceutically acceptable excipient or carrier. In some embodiments, the pharmaceutical composition is in a unit dosage form suitable for intratumorally or parenterally administration. In some embodiments, the unit dosage comprises from about $1\times10^3$ plaque-forming units (PFU) to about $1\times10^{10}$ PFU of the oncolytic virus per mL. In some embodiments, the unit dosage comprises from about $1\times10^5$ PFU to about $1\times10^{10}$ PFU of the oncolytic virus per mL. In some embodiments, a weight ratio between said oncolytic virus and said nucleocytoplasmic transport inhibitor is from about $1\times10^9$ to about $1\times10^{-9}$.

BRIEF DESCRIPTION OF THE DRAWINGS

FIG. 3A shows that PANC-1 cells were pre-treated with different concentrations of Leptomycin B for 1 h and infected with vMyx-GFP-Tdtomato at an MOI of 5.0 in the presence of the inhibitor, and fluorescence images were taken at 48 h post infection using a fluorescence microscope. FIG. 3B shows that PANC-1 cells were pre-treated with different concentration of Leptomycin B for 1 h. The cells were then infected with vMyx-GFP-TdTomato at an MOI of 5.0 or 0.5 for 1 h. After 1 h the un-adsorbed viruses were removed, and then the cells were washed and incubated with media in the presence of the inhibitor. The infected cells were harvested at 48 h or 72 h post infection and virus titers were determined following serial dilutions onto RK13 cells.

FIG. 4A shows that MDA-MB-435 cells were pre-treated with different concentrations of Leptomycin B for 1 h and infected with vMyx-GFP-Tdtomato at an MOI of 5.0 in the presence of the inhibitor, and fluorescence images were taken at 48 h post infection using a fluorescence microscope. FIG. 4B shows that MDA-MB-435 cells were pre-treated with different concentration of Leptomycin B for 1 h, and then the cells were infected with vMyx-GFP-TdTomato at an MOI of 5.0 or 0.5 for 1 h. After 1 h the un-adsorbed viruses were removed, and then the cells were washed and incubated with media in the presence of the inhibitor. The infected cells were harvested at 48 h or 72 h post infection and virus titers were determined following serial dilutions onto RK13 cells.

FIG. 5A shows HT29 cells and FIG. 5B shows PANC-1 cells (20,000 cells in 100 ul medium/well) were cultured overnight in an opaque-walled 96 well plate. The cells were then treated with different concentrations of Leptomycin B for 1 h and infected with vMyx-GFP at an MOI of 5.0 in the presence of the inhibitor. Cell viability was determined by measuring the level of ATP at 64 h (FIG. 5A) and 40 h (FIG. 5B) post infection.

DETAILED DESCRIPTION

Figures 1A, 1B:
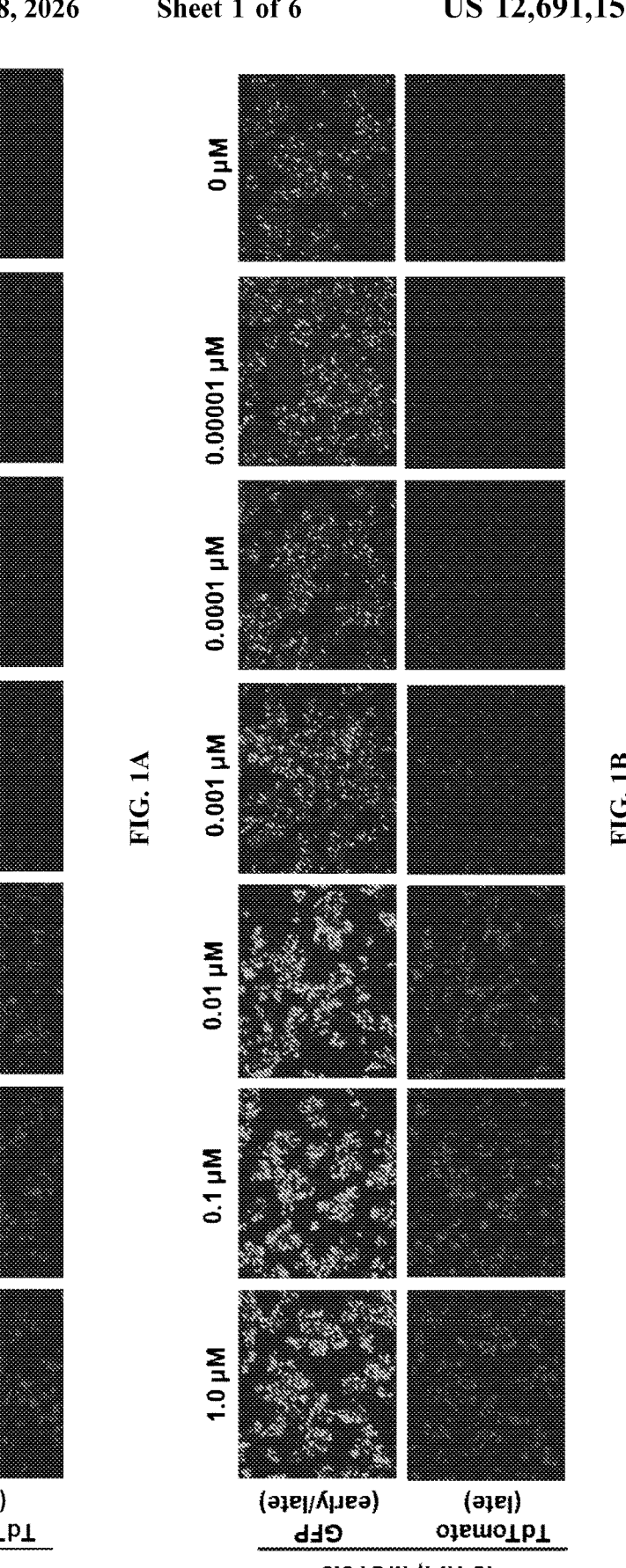
FIG. 1A and FIG. 1B illustrates the treatment of human colorectal adenocarcinoma cell line HT29 with nucleocytoplasmic transport inhibitor Leptomycin B enhanced MYXV early (GFP) and late (TdTomato) gene expression levels. HT29 cells were pre-treated with different concentrations of Leptomycin B for 1 h and infected with vMyx-GFP-Tdtomato at an MOI of 5.0 (FIG. 1A) or 0.5 (FIG. 1B) in the presence of the inhibitor, and fluorescence images were taken at 24 h (FIG. 1A) and 48 h (FIG. 1B) post infection (HPI) using a fluorescence microscope.

Viruses naturally exploit permissive cells for infection and replication; however, not all tumor cells are permissive for oncolytic virus infection. The present disclosure involves the surprising finding that treating nonpermissive cancer cells with agents, such as one or more nucleocytoplasmic transport inhibitors, can convert the nonpermissive cell into a permissive cell, promoting replication of the oncolytic virus in the cancer cells, thereby enhancing cancer cell killing.

Use of a nucleocytoplasmic transport inhibitor, as demonstrated herein, can help enhance oncolytic virus gene expression and replication in cancer cells that are normally not susceptible to infection by the oncolytic virus (i.e., not susceptible to oncolytic virus infection in the absence of the nucleocytoplasmic transport inhibitor). Addition of the nucleocytoplasmic transport inhibitor also can enhance production of oncolytic virus progeny, or proliferation of oncolytic viruses in host cells that are normally not susceptible to infection. The surprising effects of the nucleocytoplasmic transport inhibitor on nonpermissive cancer cells can translate into an enhanced cancer cell killing effect when the nucleocytoplasmic transport inhibitor is used in combination with the oncolytic virus, thus providing a more effective method for treating cancer.

The present disclosure provides methods of treating cancer, for example, cancers that are not otherwise susceptible or have low susceptibility to oncolytic viral infection, by administering an oncolytic virus and a nucleocytoplasmic transport inhibitor. Also provided herein are methods of converting a nonpermissive cancer cell to a permissive cancer cell and methods of killing a cancer cell by contacting the cancer cell with an oncolytic virus and a nucleocytoplasmic transport inhibitor. Further provided herein are pharmaceutical compositions comprising an oncolytic virus and a nucleocytoplasmic transport inhibitor.

Unless otherwise explained, all technical and scientific terms used herein have the same meaning as commonly understood by one of ordinary skill in the art to which this disclosure belongs. Although methods and materials similar or equivalent to those described herein can be used in the practice or testing of this disclosure, suitable methods and materials are described below. In addition, the materials, methods, and examples are illustrative only and not intended to be limiting.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

The term "about" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, within 5-fold, or within 2-fold, of a value.

As used herein, "one or more" or at least one can mean one, two, three, four, five, six, seven, eight, nine, ten, or more, up to any number.

As used herein, the term "comprises" or "comprising" means "includes." Hence "comprising A or B" means including A, B, or A and B. " Comprise" and variations of the term, such as "comprising", "comprises" and "comprised", as used herein, is meant that various additional components or steps can be conjointly employed.

An "effective amount" refers to an amount of a compound or composition that is sufficient to produce a desired effect, for example an increase in the production of a poxvirus. In this example, the effective amount will vary with the type of cell and the particular agent administered, the duration of the treatment, the nature of any concurrent treatment, and like factors within the knowledge and expertise of those skilled in the art.

The term "permissive" as used herein refers to whether the cell is prone to infection by the virus described in the application. As used herein, the term "susceptible to infection" refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

The term a "host cell" as used herein should be understood broadly to cover without any limitation concerning particular organization in tissue, organ, or isolated cells. Such cells may be of a unique type of cells or a group of different types of cells such as cultured cell lines, primarily cells and dividing cells. Examples of host cells can include but are not limited to prokaryotic cells, lower eukaryotic cells such as yeast and other eukaryotic cells such as insect cells such as insect cells, and mammalian (human or non-human) cells as well as cells capable of producing the oncolytic virus. A host cell can be a cancer cell, for example, a cancer cell within an organism.

A "nucleocytoplasmic transport inhibitor" is an agent that inhibits transport of molecules through the nuclear export pathway. The term "nucleocytoplasmic transport inhibitor" is used interchangeably with "nuclear export inhibitor." Examples of nucleocytoplasmic transport inhibitor include but are not limited to Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor.

A "virus" is a microscopic infectious organism that reproduces inside living cells. A virus can consist essentially of a core of a single nucleic acid surrounded by a protein coat, and has the ability to replicate only inside a living cell. "Viral replication" is the production of additional virus by the occurrence of at least one viral life cycle. A virus may subvert the host cell's normal functions, causing the cell to behave in a manner determined by the virus. For example, a viral infection may result in a cell producing a cytokine, or responding to a cytokine, when the uninfected cell does not normally do so. The term "replication-competent" as used herein refers to a virus that is capable of infecting and replicating within a particular host cell.

A "poxvirus" is a virus from the Poxviridae family. Poxviruses are double-stranded DNA viruses that are capable of infecting both vertebrates and invertebrates. Poxviruses include, for example, species and genera of viruses that are classified as being a part of the Chordopoxvirinae subfamily such as *Orthopoxvirus, Parapoxvirus, Avipoxvirus, Capripoxvirus, Leporipoxvirus, Suipoxvirus, Molluscipoxvirus*, and *Yatapoxvirus* genera, and the Entomopoxvirinae subfamily, including *Alphaentomopoxvirus, Betaentomopoxvirus*, and *Gammaentomopoxvirus* genera.

"Contacting" means placement in direct physical association. Contacting includes contact between a molecule, such as an inhibitor and a cell, for example by placing an agent in direct physical association with a cell, such as in culture with a cell. In some embodiments, contacting or exposing an agent to a cell includes placing the agent in the growth media of the cell.

"Inhibit" means to reduce to a measurable extent, for example, to reduce transport in the nuclear export pathway. An "inhibitor" is a substance capable of inhibiting to some measurable extent, for example, transport in the nuclear export pathway.

The terms "treat," "treated," "treating," "treatment," and the like are meant to encompasses prophylaxis (e.g., preventive measure in a subject at risk of having the pathological condition to be treated) and/or therapy (e.g. in a subject diagnosed as having the pathological condition). The result of the treatment is to slow down, cure, reduce, control, or ameliorate a disorder and/or symptoms associated therewith. "Treating" includes the concepts of "alleviating", which refers to lessening the frequency of occurrence or recurrence, or the severity, of any symptoms or other ill effects related to a disorder and/or the associated side effects. The term "treating" also encompasses the concept of "managing" which refers to reducing the severity of a particular disease or disorder in a patient or delaying its recurrence, e.g., lengthening the period of remission in a patient who had suffered from the disease. The term "treating" further encompasses the concept of "prevent," "preventing," and "prevention," as previously stated. It is appreciated that, although not precluded, treating a disorder or condition does not require that the disorder, condition, or symptoms associated therewith be completely eliminated.

A "pharmaceutically acceptable excipient or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

Oncolytic Viruses

Oncolytic virus described herein encompasses virus capable of selectively replicating in dividing cells (e.g., a proliferative cell such as a cancer cell) with the aim of slowing the growth and/or lysing said dividing cell, either in vitro or in vivo, while showing no or minimal replication in non-dividing cells. Typically, an oncolytic virus contains a viral genome packaged into a viral particle or virion and is infectious (i.e. capable of infecting and entering into a host cell or subject). As used herein, this term encompasses DNA or RNA vectors (depending on the type of virus) as well as viral particles generated thereof.

In some embodiments, oncolytic viruses are mammalian viruses that are designed and/or selected for their ability to selectively infect and kill transfected cancer cells, and by their ability to activate the host immune system against not only the virus, but also tumor antigens.

In some embodiments, the oncolytic virus is a virus from the Poxviridae family or is derived from the Poxviridae family. Members of Poxviridae family of viruses are a diverse group of large, complex double-stranded DNA viruses that can replicate in the cytoplasm of infected cells. The genomes of most poxviruses are about 150,000 to 300,000 base pairs in length and encode approximately 150 to 300 proteins. About half of these viral proteins are highly conserved between different poxvirus members and perform essential functions like cell binding and entry, genome replication, transcription and virion assembly. Other viral proteins are involved in evading many host defense functions. The poxviral genes can be expressed in distinct phases. For example, the early gene products can include proteins that are necessary for viral DNA replication and are expressed before the DNA is replicated. On the other hand, the intermediate/late gene products expressed during or after DNA replication can include the structural proteins required for virion maturation. All the steps of this complex viral replication process (starting from un-coating the genome, early gene expression, DNA replication, late gene expression and an even more complex virion maturation processes) can occur exclusively in the cytoplasm of the infected cells.

Poxviruses are large DNA viruses which can replicate exclusively within the cytoplasm of the infected cells. They can encode all of the proteins required for DNA and mRNA synthesis. Apart from viral proteins involved in poxvirus replication, about half of the poxvirus genome encode proteins that have been shown to be required for the inhibition or manipulation of diverse intracellular anti-viral signaling pathways functioning in the cytoplasm and nucleus. However, there is evidence that host cell proteins from cytoplasm and nuclear compartments participate in at least some steps of poxvirus replication. Many diverse cellular proteins and signaling pathways have been implicated in defending the cell against the infection and replication of poxviruses. This is why more than half of the genome-encoded poxvirus proteins are involved in the specific inhibition or modulation of these host anti-viral pathways. In some cases, the virus-encoded proteins function in a host specific manner and determine whether a given poxvirus will be able to successfully infect and replicate in a specific species of host. Members of poxviruses, for example, Myxoma virus (MYXV), a Leporipoxvirus, and vaccinia virus (VACV), an orthopoxvirus, could be developed as oncolytic viruses for the treatment of human cancers.

In certain embodiments, the poxvirus of interest is genetically modified. For example, the poxvirus of interest can be modified to carry any other gene, such as a therapeutic gene, and/or to delete or disrupt one or more endogenous viral genes. In the case of viruses modified to treat cancer, the gene would typically be selected to enhance the anticancer effect of the treatment. Such a gene may be a gene that is involved in triggering apoptosis, or is involved in targeting the infected cell for immune destruction, such as a gene that repairs a lack of response to interferon, or that results in the expression of a cell surface marker that stimulates an antibody response, such as a bacterial cell surface antigen. The virus may also be modified to express genes involved in shutting off the neoplastic or cancer cell's proliferation and growth, thereby preventing the cells from dividing. As well, the virus may be modified to include therapeutic genes, such as genes involved in the synthesis of chemotherapeutic agents, or it may be modified to have increased replication levels in cells of the particular species from which the cells to be inhibited or killed are derived, for example, human cells.

In some embodiments, the oncolytic virus is a virus from Chordopoxvirinae subfamily or Entomopoxvirinae subfamily or is derived from Chordopoxvirinae subfamily or Entomopoxvirinae subfamily. In some embodiments, the oncolytic virus is from a genus that is *Orthopoxvirus, Cervidpoxvirus, Parapoxvirus, Avipoxvirus, Capripoxvirus, Leporipoxvirus, Suipoxvirus, Molluscipoxvirus, Yatapoxvirus, Alphaentomopoxvirus, Betaentomopoxvirus,* or *Gammaentomopoxvirus.* In some embodiments, the oncolytic virus is derived from a virus from a genus that is *Orthopoxvirus, Cervidpoxvirus, Parapoxvirus, Avipoxvirus, Capripoxvirus, Leporipoxvirus, Suipoxvirus, Molluscipoxvirus, Yatapoxvirus, Alphaentomopoxvirus, Betaentomopoxvirus,* or *Gammaentomopoxvirus.* In some embodiments, the oncolytic virus is from genus *Orthopoxvirus* or is derived from a virus of the genus *Orthopoxvirus.* In some embodiments, the oncolytic virus is a vaccinia virus or is derived from a vaccinia virus. In some embodiments, the vaccinia virus is a vaccinia virus strain selected from the group consisting of Lister, Wyeth, Western Reserve, Modified Vaccinia virus Ankara, and LC16m series. In some embodiments, the oncolytic virus is a Raccoonpox virus or is derived from a Raccoonpox virus. In some embodiments, the oncolytic virus is from genus *Cervidpoxvirus* or is derived from a virus of the genus *Cervidpoxvirus.* In some embodiments, the oncolytic virus is an Orf virus or is derived from an Orf virus. In some embodiments, the oncolytic virus is from genus *Parapoxvi-* rus or is derived from a virus of the genus *Parapoxvirus*. In some embodiments, the oncolytic virus is from genus *Avipoxvirus* or is derived from a virus of the genus *Avipoxvirus*. In some embodiments, the oncolytic virus is from genus *Capripoxvirus* or is derived from a virus of the genus *Capripoxvirus*. In some embodiments, the oncolytic virus is from genus *Suipoxvirus* or is derived from a virus of the genus *Suipoxvirus*. In some embodiments, the oncolytic virus is from genus *Molluscipoxvirus* or is derived from a virus of the genus *Molluscipoxvirus*. In some embodiments, the oncolytic virus is from genus *Yatapoxvirus* or is derived from a virus of the genus *Yatapoxvirus*. In some embodiments, the oncolytic virus is from genus *Alphaentomopoxvirus* or is derived from a virus of the genus *Alphaentomopoxvirus*. In some embodiments, the oncolytic virus is from genus *Betaentomopoxvirus* or is derived from a virus of the genus *Betaentomopoxvirus*. In some embodiments, the oncolytic virus is from genus *Gammaentopoxvirus* or is derived from a virus of the genus *Gammaentopoxvirus*. In some embodiments, the oncolytic virus is from genus *Leporipoxvirus* or is derived from a virus of the genus *Leporipoxvirus*. In some embodiments, the oncolytic virus is a myxoma virus (MYXV) or is derived from a MYXV.

MYXV is potentially well suited as a therapeutic virus against solid cancers, such as osteosarcoma, because of its unique biology. MYXV is a member of the family poxviridae and genus *Leporipoxvirus*. Thus, in certain embodiments, a poxvirus of interest is an oncolytic virus candidate. In certain embodiments, the poxvirus of interest is a Leporipoxvirus, such as a myxoma virus. In certain embodiments, the poxvirus of interest is an Orthopoxvirus, such as a vaccinia virus, including different strains of vaccinia virus such as Lister, Wyeth, Western Reserve (WR), Modified Vaccinia virus Ankara (MVA), and LC16m series; and Raccoonpox virus (RCNV). In certain embodiments, the poxvirus of interest is a Yatapoxvirus, such as a Tanapoxvirus (TPV) or Yaba-like disease virus (YLDV). In certain embodiments, the poxvirus of interest is a capripox virus, such as Orf virus.

MYXV is a rabbit-specific pathogen. The MYXV may be any virus that belongs to the Leporipoxvirus species of poxviruses that is replication-competent. In some embodiments, the MYXV is a wild-type strain of MYXV or is derived from a wild-type strain of MYXV. In some embodiments, the MYXV is a genetically modified strain of MYXV or is derived from a genetically modified strain of MYXV. In some instances, the MYXV is Lausanne strain or is derived from Lausanne strain. In some instances, the MYXV is a South American MYXV strain that circulates in Sylvilagus brasiliensis or is derived from a South American MYXV strain that circulates in Sylvilagus brasiliensis. In some instances, the MYXV is a Californian MYXV strain that circulates in Sylvilagus bachmani or is derived from a Californian MYXV strain that circulates in Sylvilagus bachmani. In some instances, the MYXV is 6918, an attenuated Spanish field strain that comprises modifications in genes M009L, M036L, M135R, and M148R (GenBank Accession number EU552530 which is hereby incorporated by reference as provided by GenBank on Jul. 27, 2019) or is derived from 6918. In some instances, the MYXV is 6918VP60-T2 (GenBank Accession Number EU552531 which is hereby incorporated by reference as provided by GenBank on Jul. 27, 2019) or is derived from 6918VP60-T2. In some instances, the MYXV is a strain termed the Standard laboratory Strain (SLS) or is derived from SLS.

In some instances, the MYXV comprises at least 80%, at least 90%, at least 95%, at least 96%, at least 97%, at least 98%, or at least 99%, such as between 95% and 98%, 95% and 99%, including 90%, 91%, 92%, 93%, 94%, 95%, 96%, 97%, 98%, 99% sequence identity to a sequence disclosed in Cameron, et al., "The complete DNA sequence of Myxoma Virus," Virology 264: 298-318 (1999) (which is herein incorporated by reference in its entirety). In some cases, the MYXV comprises the sequence disclosed in Cameron, et al., "The complete DNA sequence of Myxoma Virus," Virology 264: 298-318 (1999).

In some embodiments, the MYXV is non-pathogenic in humans (e.g., immunocompetent humans) but able to infect and kill a wide range of human cancer cells derived from different tissues. In normal primary human cells, the replication of MYXV can be restricted by multiple factors such as, for example, the cellular binding determinants, the intracellular anti-viral signaling pathways and type I IFN and/other cytokines mediated cellular anti-viral states. In human cancer cells, these self-defense cell pathways are commonly defective. MYXV replication in some human cancer cells can depend on cellular RNA helicase family proteins. Without wishing to be bound by theory, RNA helicases which shuttle between nuclear and cytoplasmic compartments of cells may influence MYXV replication in virus-infected cells. Beside RNA helicases, other nuclear proteins may contribute to the replication cycle of MYXV and other poxviruses. For example, nuclear proteins might affect the replication efficiency of poxviruses in transformed human host cell lines.

In some embodiments, the oncolytic virus is from a virus family consisting of: Poxviridae, Herpesviridae, Reoviridae, Paramyxoviridae, Retroviridae, Adenoviridae, Rhabdoviridae, Picornaviridae, Parvoviridae, and Picornaviridae, or is derived from a virus family consisting of: Poxviridae, Herpesviridae, Reoviridae, Paramyxoviridae, Retroviridae, Adenoviridae, Rhabdoviridae, Picornaviridae, Parvoviridae, and Picornaviridae. In some embodiments, the oncolytic virus is from the Herpesviridae family or is derived from the Herpesviridae family. In some embodiments, the oncolytic virus is from the Reoviridae family or is derived from the Reoviridae family. In some embodiments, the oncolytic virus is from the Paramyxoviridae family or is derived from Paramyxoviridae family. In some embodiments, the oncolytic virus is from the Retroviridae family or is derived from is from the Retroviridae family. In some embodiments, the oncolytic virus is from the Adenoviridae family or is derived from the Adenoviridae family. In some embodiments, the oncolytic virus is from the Rhabdoviridae family or is derived from the Rhabdoviridae family. In some embodiments, the oncolytic virus is from the Picornaviridae family or is derived from the Picornaviridae family. In some embodiments, the oncolytic virus is from the Parvoviridae family or is derived from the Parvoviridae family. In some embodiments, the oncolytic virus is from the Picornaviridae family. In some embodiments, the oncolytic virus is from a genus that is *Simplexvirus, Rubulavirus,* or *Senecavirus* or is derived from a genus that is *Simplexvirus, Rubulavirus,* or *Senecavirus*. In some embodiments, the oncolytic virus is from genus *Simplexvirus* or is derived from genus *Simplexvirus*. In some embodiments, the oncolytic virus is from genus *Rubulavirus* or is derived from genus *Rubulavirus*. In some embodiments, the oncolytic virus is from genus *Senecavirus* or is derived from genus *Senecavirus*. In some embodiments, the oncolytic virus is from a species of virus that is Measles, Fowlpox, Vesicular Stomatitis Virus, Mumps rubulavirus, Coxsackie Virus, and Vaccinia or is derived from a species of virus that is Measles, Fowlpox, Vesicular Stomatitis Virus, Mumps rubulavirus, Coxsackie Virus, and Vaccinia. In some embodiments, the oncolytic virus is a Measles virus or is derived from a Measles virus. In some embodiments, the oncolytic virus is a Fowlpox virus or is derived from a Fowlpox virus. In some embodiments, the oncolytic virus is a Vesicular Stomatitis Virus or is derived from a Vesicular Stomatitis Virus. In some embodiments, the oncolytic virus is a Mumps rubulavirus or is derived from Mumps rubulavirus. In some embodiments, the oncolytic virus is a Coxsackie Virus or is derived from is a Coxsackie Virus. In some embodiments, the oncolytic virus is a Vaccinia virus or is derived from is a Vaccinia virus.

In some embodiments, the oncolytic virus is replication-competent. In some embodiments, the oncolytic virus is from a wild-type strain, or is derived from a wild-type strain. In some embodiments, the oncolytic virus is from a genetically modified strain, or is derived from a genetically modified strain. In some embodiments, the oncolytic virus is genetically modified. In some embodiments, the oncolytic virus is non-pathogenic in humans but able to infect and kill a wide range of human cancer cells derived from different tissues. In some embodiments, the nucleic acid sequence of the oncolytic virus comprises at least 90%, at least 95%, at least 96%, at least 97%, at least 98%, or at least 99%, such as between 95% and 98%, 95% and 99%, including 90%, 91%, 92%, 93%, 94%, 95%, 96%, 97%, 98%, and 99% sequence identity to a nucleic acid sequence of a wild type virus sequence.

Nucleocytoplasmic Transport Inhibitor

As disclosed herein, nucleocytoplasmic transport inhibitors can enhance virus replication and reduce cell viability for cancer cells such as nonpermissive cancer cells. In certain embodiments, the nucleocytoplasmic transport inhibitor is a selective inhibitor. In certain embodiments, the nucleocytoplasmic transport inhibitor is non-selective. In some embodiments, the described nucleocytoplasmic transport inhibitors are agents that are capable of interfering with nucleocytoplasmic trafficking. In some embodiments, the agents inhibit nucleocytoplasmic transport by interfering with protein trafficking. In some embodiments, the agents comprise Trifuoperazine hydrochloride, W13, ETP-45648, Vinblastine, Akt inhibitor X, INCAs, SMIP001/004, Resveratrol, Elliticine, WGA, cSN50 peptide, bimax1/2 peptide, Leptomycin B, Anguinomycins, Goniothalamin, Ratjadone, Valtrate, Acetoxychavicol acetate, 15d-PGJ2, Peumusolide A, PKF050-638, KOS-2464, CBS9106, or a combination thereof. In some embodiments, the nucleocytoplasmic transport inhibitor comprises a small molecule compound. In some embodiments, the nucleocytoplasmic transport inhibitor comprises a natural compound such as Ratjadone, valtrate and acetoxychavicol acetate. In some embodiments, the nucleocytoplasmic transport inhibitor comprises a selective inhibitor of the nuclear export (SINE). In some embodiments, the nucleocytoplasmic transport inhibitor comprises a reversible nuclear export inhibitor such as CBS9106.

In certain embodiments, the nucleocytoplasmic transport inhibitor comprises one or more of Leptomycin A, Leptomycin B, Ratjadone A, B, C and D, Anguinomycin A, Goniothalamin, piperlongumine, plumbagin, curcumin, valtrate, acetoxychavicol acetate, prenylcoumarin osthol, or synthetic nucleocytoplasmic transport inhibitors such as KOS 2464, PKF050-638 (N-azolylacrylate analog), CBS9106, Selinexor, and those found in Mathew and Ghildyal, CRM1 inhibitors for antiviral therapy, Frontiers in Microbiology 2017, Vol 8, article 1171, which is incorporated herein by reference. In some embodiments, the nucleocytoplasmic transport inhibitor comprises Leptomycin A. In some embodiments, the nucleocytoplasmic transport inhibitor comprises Leptomycin B. In some embodiments, the nucleocytoplasmic transport inhibitor comprises Ratjadone A. In some embodiments, the nucleocytoplasmic transport inhibitor comprises Ratjadone B. In some embodiments, the nucleocytoplasmic transport inhibitor comprises Ratjadone C. In some embodiments, the nucleocytoplasmic transport inhibitor comprises Ratjadone D. In some embodiments, the nucleocytoplasmic transport inhibitor comprises Anguinomycin A. In some embodiments, the nucleocytoplasmic transport inhibitor comprises Goniothalamin. In some embodiments, the nucleocytoplasmic transport inhibitor comprises piperlongumine. In some embodiments, the nucleocytoplasmic transport inhibitor comprises plumbagin. In some embodiments, the nucleocytoplasmic transport inhibitor comprises curcumin. In some embodiments, the nucleocytoplasmic transport inhibitor comprises valtrate. In some embodiments, the nucleocytoplasmic transport inhibitor comprises acetoxychavicol acetate. In some embodiments, the nucleocytoplasmic transport inhibitor comprises prenylcoumarin osthol. In some embodiments, the nucleocytoplasmic transport inhibitor comprises KOS 2464. In some embodiments, the nucleocytoplasmic transport inhibitor comprises PKF050-638. In some embodiments, the nucleocytoplasmic transport inhibitor comprises CBS9106. In some embodiments, the nucleocytoplasmic transport inhibitor comprises Selinexor. In some embodiments, the nucleocytoplasmic transport inhibitor is Leptomycin B.

Method of Treatment

Use of a nucleocytoplasmic transport inhibitor surprisingly helps convert cancer cells that are not susceptible to infection by the oncolytic virus (e.g., MYXV) to cancer cells that are susceptible to infection by the oncolytic virus, i.e., induces susceptibility of a cancer cell to infection by the oncolytic virus. Addition of the nucleocytoplasmic transport inhibitor increases the susceptibility of a cancer cell to infection by an oncolytic virus. The nucleocytoplasmic transport inhibitor can be used to make a cancer cell that has low susceptibility to infection by oncolytic virus into a cancer cell that has high susceptibility to infection by oncolytic virus. Therefore, the nucleocytoplasmic transport inhibitor can be administered in combination with oncolytic virus to improve the efficacy of the oncolytic virus in treating cancer and killing tumor cells.

Disclosed herein are methods of using an oncolytic virus and compositions comprising an oncolytic virus. Disclosed herein, in some embodiments, are methods for treating cancer by administering to a subject with a therapeutically effective amount of an oncolytic virus (e.g., MYXV or VACV) and a nucleocytoplasmic transport inhibitor. In one aspect, disclosed herein are methods of converting a non-permissive cell to a permissive cell comprising: contacting a cancer cell that is nonpermissive to an oncolytic virus with the oncolytic virus and a nucleocytoplasmic transport inhibitor, thereby converting said cancer cell. In another aspect, disclosed herein are methods of killing a cancer cell comprising: contacting a cancer cell with an oncolytic virus and a nucleocytoplasmic transport inhibitor, thereby killing said cancer cell. Accordingly, in some embodiments, this disclosure provides methods of increasing virus replication in a nonpermissive cancer cell by treating the nonpermissive cell with a nucleocytoplasmic transport inhibitor.

Some embodiments relate to a method of enhancing a susceptibility of a cancer cell to infection by an oncolytic virus, comprising: contacting the cancer cell to an oncolytic virus and a nucleocytoplasmic transport inhibitor. Some embodiments relate to a method of making a cancer cell susceptible to infection by an oncolytic virus, comprising contacting the cancer cell to the oncolytic virus and a nucleocytoplasmic transport inhibitor.

Some embodiments relate to a method of increasing proliferation of an oncolytic virus in a cancer cell that is not susceptible to infection by the oncolytic virus, comprising: contacting the cancer cell to an oncolytic virus and a nucleocytoplasmic transport inhibitor.

The oncolytic virus and the nucleocytoplasmic transport inhibitor can be administered together or separately. In some embodiments, the oncolytic virus and the nucleocytoplasmic transport inhibitor can be administered together. In some embodiments, the oncolytic virus and the nucleocytoplasmic transport inhibitor can be administered separately. When the oncolytic virus and the nucleocytoplasmic transport inhibitor are administered separately, the oncolytic virus can be administered prior to the nucleocytoplasmic transport inhibitor. When the oncolytic virus and the nucleocytoplasmic transport inhibitor are administered separately, the oncolytic virus can be administered after the nucleocytoplasmic transport inhibitor.

In some embodiments, the cancer cell, e.g., the nonpermissive cancer cell, is an animal cell such as a mammalian cell. In some embodiments, the cancer cell, e.g., the non-permissive cancer cell, is a human cell. In certain embodiments, the cell is an immortalized human or primate cell. In certain embodiments, the cell is from a cancer cell line. In some embodiments, the cell is a Human A549 cell, HeLa cell, 239 cell, or primate Vero cell. The cancer cell can be an in vivo cell, an in vitro cell, or an ex vivo cell. In some embodiments, the cancer cell is a cell of a cancer tissue of the subject to be treated.

The cancer can be a solid tumor or a blood tumor. In some embodiments, the cancer is leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or a solid tumor. In some embodiments, the cancer is a solid tumor. In some embodiments, the solid tumor is a sarcoma or a carcinoma. In some embodiments, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, or retinoblastoma. In some embodiments, the solid tumor is colorectal adenocarcinoma, pancreatic cancer, or melanoma. In some embodiments, the solid tumor is a bone cancer such as chondrosarcoma, Ewing sarcoma, and osteosarcoma. In some embodiments, the solid tumor is osteosarcoma.

The oncolytic virus and the nucleocytoplasmic transport inhibitor can be administered to the subject with cancer simultaneously or sequentially. In some embodiments, the oncolytic virus and the nucleocytoplasmic transport inhibitor are administered to the subject simultaneously. In some embodiments, the oncolytic virus and the nucleocytoplasmic transport inhibitor are pre-mixed before their administration to the subject. In some embodiments, the oncolytic virus and the nucleocytoplasmic transport inhibitor are administered to the subject separately. In some embodiments, the oncolytic virus is administered before the nucleocytoplasmic transport inhibitor. In some embodiments, the oncolytic virus is administered after the nucleocytoplasmic transport inhibitor. In some embodiments, the method comprises contacting the cancer cell or cancer tissue with the oncolytic virus and the nucleocytoplasmic transport inhibitor simultaneously or sequentially. In some embodiments, the cancer cell or cancer tissue is contacted with the oncolytic virus before its contact with the nucleocytoplasmic transport inhibitor. In some embodiments, the cancer cell or cancer tissue is contacted with the nucleocytoplasmic transport inhibitor before its contact with the oncolytic virus. In some embodiments, the method comprises contacting the cancer cell or cancer tissue with a pre-mix of the oncolytic virus and the nucleocytoplasmic transport inhibitor. In some embodiments, the cancer cell or cancer tissue is contacted with the oncolytic virus and the nucleocytoplasmic transport inhibitor separately.

In some embodiments, the method comprises pre-treating the cancer cell or cancer tissue with the nucleocytoplasmic transport inhibitor. In some embodiments, the cancer cell or cancer tissue is pre-treated with the nucleocytoplasmic transport inhibitor for at least 1 minute, at least 2 minutes, at least 5 minutes, at least 10 minutes, at least 30 minutes, at least 1 hour, at least 2 hours, at least 6 hours, at least 12 hours, at least 24 hours, or at least 1 week before contacting the cell or tissue with the oncolytic virus. In some embodiments, the cancer cell or cancer tissue is pre-treated with the nucleocytoplasmic transport inhibitor for at most 1 minute, at most 2 minutes, at most 5 minutes, at most 10 minutes, at most 30 minutes, at most 1 hour, at most 2 hours, at most 6 hours, at most 12 hours, at most 24 hours, or at most 1 week before contacting the cell or tissue with the oncolytic virus. In some embodiments, the cancer cell or cancer tissue is pre-treated with the nucleocytoplasmic transport inhibitor for a period of from about 1 minute to about 1 day, from about 5 minutes to about 12 hours, from about 10 minutes to about 2 hours, or from about 30 minutes to about 90 minutes before contacting the cell or tissue with the oncolytic virus. In some embodiments, the cancer cell or cancer tissue is pre-treated with the nucleocytoplasmic transport inhibitor for about 1 hour before contacting the cell or tissue with the oncolytic virus.

In one aspect, described herein are methods comprising administering the oncolytic virus to a cell that is autologous, allogeneic, or heterologous to a subject with cancer. The oncolytic virus can be administered in vivo or ex vivo. In some embodiments, the method comprises administering the oncolytic virus to an autologous cell ex vivo. In some embodiments, the method comprises administering the oncolytic virus to an allogeneic cell ex vivo. In some embodiments, the method comprises administering the oncolytic virus to a heterologous cell ex vivo. In some embodiments, the autologous, allogeneic, or heterologous cell is a bone marrow cell or a macrophage cell. In some embodiments, the autologous, allogeneic, or heterologous cell is a stem cell. In some embodiments, the autologous, allogeneic, or heterologous cell is any cell non-permissive to the oncolytic virus. In some embodiments, the autologous, allogeneic, or heterologous cell is any cell permissive to the oncolytic virus. In some embodiments, the autologous, allogeneic, or heterologous cell is a healthy cell. In some embodiments, the administering comprises contacting the oncolytic virus with the autologous, allogeneic, or heterologous cell. In some embodiments, the method comprises administering said autologous, allogeneic, or heterologous cell into a subject. In some embodiments, the method comprises injecting said autologous, allogeneic, or heterologous cell into a subject. In some embodiments, the method comprises administering the nucleocytoplasmic transport inhibitor prior to the administration of the autologous, allogeneic, or heterologous cell. In some embodiments, the method comprises administering the nucleocytoplasmic transport inhibitor after the administration of the autologous, allogeneic, or heterologous cell.

In some embodiments, the method comprises administering the oncolytic virus, the nucleocytoplasmic transport inhibitor, or both to the subject for a period of time. In some embodiments, the period of time is at least 1 day, at least 2 days, at least 3 days, at least 1 week, at least 2 weeks, at least 3 weeks, at least 4 weeks, at least 1 month, at least 3 months, at least 6 months, or at least 1 year. In some embodiments, the period of time is at most 1 day, at most 2 days, at most 3 days, at most 1 week, at most 2 weeks, at most 3 weeks, at most 4 weeks, at most 1 month, at most 3 months, at most 6 months, at most 1 year, or at most 10 years. In some embodiments, the period of time is from about 1 day to about 1 year, from about 1 month to about 12 months, or from 1 month to about 6 months. In some embodiments, the method comprises administering the oncolytic virus, the nucleocytoplasmic transport inhibitor, or both to the subject twice a week, once a week, once every two weeks, once every three weeks, once every four weeks, once a month, or once every two months. In some embodiments, the oncolytic virus, the nucleocytoplasmic transport inhibitor, or both are administered to the subject from 1 to 4 weeks apart, for examples, about 1 week apart, about 2 weeks apart or about 3 weeks apart.

In some embodiments, the method comprises administering the oncolytic virus, the nucleocytoplasmic transport inhibitor, or both according to an initial dose schedule and a subsequent dose schedule. In some embodiments, the initial dose schedule comprises a different dosing schedule from the subsequent dose schedule. In some embodiments, the initial dose schedule comprises a less frequent administration than the subsequent dose schedule. In some embodiments, the initial dose schedule comprises 1 to 10 treatments, such as 1 to 4 treatments or 2 to 3 treatments of the oncolytic virus, the nucleocytoplasmic transport inhibitor, or both. In some embodiments, each treatment of the oncolytic virus, the nucleocytoplasmic transport inhibitor, or both is administered from 1 week to about 6 weeks apart according to the initial dose schedule. In some embodiments, each treatment of the oncolytic virus, the nucleocytoplasmic transport inhibitor, or both is administered about 1 week apart, about 2 weeks apart, about 3 weeks apart, or about 4 weeks apart according to the initial dose schedule. In some embodiments, each treatment of the oncolytic virus, the nucleocytoplasmic transport inhibitor, or both is administered from 1 week to about 6 weeks apart according to the subsequent dose schedule. In some embodiments, each treatment of the oncolytic virus, the nucleocytoplasmic transport inhibitor, or both is administered about 1 week apart, about 2 weeks apart, about 3 weeks apart, or about 4 weeks apart according to the subsequent dose schedule. In some embodiments, the oncolytic virus, the nucleocytoplasmic transport inhibitor, or both are administered about 3 weeks apart in the initial dose schedule and about 2 weeks apart in the subsequent dose schedule.

In some embodiments, the method comprises a local administration to the cancer tissue to be treated. For example, in some embodiments, the oncolytic virus, the nucleocytoplasmic transport inhibitor, or both are administered locally to a cancer tissue to be treated. In some embodiments, the oncolytic virus is administered locally and the nucleocytoplasmic transport inhibitor is not administered locally. In some embodiments, the oncolytic virus, the nucleocytoplasmic transport inhibitor, or both are administered parenterally. In some embodiments, the nucleocytoplasmic transport inhibitor, or both are administered by injection. In some embodiments, the oncolytic virus, the nucleocytoplasmic transport inhibitor, or both are administered by cutaneous injection, subcutaneous injection, or injection to a nodal lesion. In some embodiments, the oncolytic virus, the nucleocytoplasmic transport inhibitor, or both are administered by an injection to the cancer tissue or a cancer organ that contains the cancer tissue.

In some embodiments, the method comprises administering a therapeutically effective amount of a nucleocytoplasmic transport inhibitor at or near the cancer tissue. In some embodiments, the method comprises contacting the cancer cell or cancer tissue with a media comprising a therapeutically effective amount of the nucleocytoplasmic transport inhibitor. In some embodiments, the method comprises incubating the cancer cell or cancer tissue with a media comprising a therapeutically effective amount of the nucleocytoplasmic transport inhibitor.

In some embodiments, a therapeutically effective amount of nucleocytoplasmic transport inhibitor is determined for a given cancer cell or cancer tissue (e.g., a given inhibitor, virus strain and host cell line). An effective amount of nucleocytoplasmic transport inhibitor can be determined, for example, by titrating the amount of the inhibitor, and quantifying the replication of viral progeny and/or cell viability as disclosed herein. In some embodiments, a therapeutically effective amount of a nucleocytoplasmic transport inhibitor comprises a concentration of about 0.000001 μM to about 100 μM, about 0.000001 μM to about 10 μM, about 0.00001 μM to about 1 μM, about 0.01 μM to about 1 μM, about 0.00001 μM to about 0.1 μM, about 0.00005 μM to about 0.05 μM, or about 0.00005 μM to about 0.005 μM. In some embodiments, a therapeutically effective amount of a nucleocytoplasmic transport inhibitor comprises a concentration of from about 0.01 μM to about 1 μM. In some embodiments, a therapeutically effective amount of a nucleocytoplasmic transport inhibitor comprises a concentration of greater than about 0.000001 μM, about 0.000005 μM, about 0.00001 μM, about 0.00005 μM, about 0.0001, about 0.0005 μM, about 0.001 μM, about 0.005 μM, about 0.01 μM, about 0.05 μM, or about 0.1 μM. In some embodiments, a therapeutically effective amount of a nucleocytoplasmic transport inhibitor comprises a concentration of no more than about 0.0005 μM, about 0.001 μM, about 0.0015 μM, about 0.002 μM, about 0.0025 μM, about 0.003 μM, about 0.0035 μM, about 0.004 μM, about 0.0045 μM, about 0.005 μM, about 0.01 μM, about 0.015 μM, about .02 μM, about 0.025 μM, about 0.03 μM, about 0.035 μM, about 0.04

μM, about 0.045 μM, about 0.05 μM, about 0.1 μM, about 0.2 μM, about 0.25 μM, about 0.3 μM, about 0.4 μM, about 0.5 μM, about 0.75 μM, about 0.9 μM, about 1 μM, about 1.25 μM, about 1.5 μM, about 1.75 μM, about 2 μM, about 3 μM, about 4 μM, about 5 μM, about 6 μM, about 7 μM, about 8 μM, about 9 μM, or about 10 μM. In some embodiments, a therapeutically effective amount of a nucleocytoplasmic transport inhibitor is between about 0.000001 μM and about 10 μM, such as about 0.0005 μM, about 0.001 μM, about 0.0015 μM, about 0.002 μM, about 0.0025 82 M, about 0.003 μM, about 0.0035 μM, about 0.004 μM, about 0.0045 μM, about 0.005 μM, about 0.01 μM, about 0.015 μM, about 0.02 μM, about 0.025 μM, about 0.03 82 M, about 0.035 μM, about 0.04 μM, about 0.045 μM, about 0.05 μM, about 0.1 μM, about 0.2 μM, about 0.3 μM, about 0.4 μM, about 0.5 μM, about 0.6 μM, about 0.7 μM, about 0.8 μM, about 0.9 μM, about 1.0 μM, about 1.1 μM, about 1.2 μM, about 1.3 μM, about 1.4 μM, about 1.5 μM, about 1.6 μM, about 1.7 μM, about 1.8 μM, about 1.9 μM, about 2.0 μM, about 3.0 μM, about 4.0 μM, and about 5.0 μM.

In some embodiments, the method comprises administering a therapeutically effective amount of the oncolytic virus (e.g., MYXV or VACV) at or near the cancer tissue. In some embodiments, the method comprises infecting the cancer cell or cancer tissue with a therapeutically effective amount of the oncolytic virus. In some embodiments, a therapeutically effective amount of the oncolytic virus is present when the cancer cell or cancer tissue is infected at an effective multiplicity of infection (MOI). In some embodiments, the method comprises contacting the cancer cell or cancer tissue with the oncolytic virus at an MOI as described herein. The MOI can be determined for a given cell or tissue, for example, by titrating the ratio of virus to the cell or tissue, and quantifying the replication of viral progeny and/or the cell viability as disclosed herein. In some embodiments, an effective MOI can minimize drug-specific cellular toxicity, while enhancing replication of the virus and reducing cancer cell viability. In some embodiments, the cancer cell is allowed to incubate with the oncolytic virus (e.g., MYXV or VACV) for a period of time to allow the virus of interest to adsorb to the surface of the cell, such as about 20 minutes to about 5 hours, for example about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 2 hours, about 2.5 hours, about 3 hours, about 3.5 hours, about 4 hours, about 4.5 hours, about 5 hours, 12 hours, 18 hours, 20 hours, 24 hours, 30 hours, 36 hours, or even longer.

In certain embodiments, the MOI of the oncolytic virus to the cancer cell or cancer tissue is between about 0.001 to 2.0 or about 0.01 and 1.0, such as about 0.001, about 0.005, 0.01, about 0.02, about 0.03, about 0.04, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1.0, about 1.1, about 1.2, about 1.3, about 1.4, about 1.5, about 1.6, about 1.7, about 1.8, about 1.9, or about 2.0. In certain embodiments, the MOI of the oncolytic virus to the cancer cell or cancer tissue is from about 0.01 to about 10, from about 0.05 to about 5, and/or ranges therebetween. In certain embodiments, the MOI of the oncolytic virus to the cancer cell or cancer tissue is about 0.05, about 0.5 or about 5. In some embodiments, the MOI of the oncolytic virus to the cancer cell or cancer tissue is at least about 0.001, at least about 0.005, at least about 0.01, at least about 0.02, at least about 0.03, at least about 0.04, at least about 0.05, at least about 0.06, at least about 0.07, at least about 0.08, at least about 0.09, at least about 0.1, at least about 0.15, at least about 0.2, at least about 0.25, at least about 0.3, at least about 0.35, at least about 0.4, at least about 0.45, at least about 0.5, at least about 0.55, at least about 0.6, at least about 0.65, at least about 0.7, at least about 0.75, at least about 0.8, at least about 0.85, at least about 0.9, at least about 0.95, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.5, at least about 3.0, at least about 4.0, at least about 5.0, or at least about 6.0. In some embodiments, the MOI of the oncolytic virus to the cancer cell or cancer tissue is at most about 0.01, at most about 0.02, at most about 0.03, at most about 0.04, at most about 0.05, t most about 0.06, at most about 0.07, at most about 0.08, at most about 0.09, at most about 0.1, at most about 0.15, at most about 0.2, at most about 0.25, at most about 0.3, at most about 0.35, at most about 0.4, at most about 0.45, at most about 0.5, at most about 0.55, at most about 0.6, at most about 0.65, at most about 0.7, at most about 0.75, at most about 0.8, at most about 0.85, at most about 0.9, at most about 0.95, at most about 1.0, at most about 1.1, at most about 1.2, at most about 1.3, at most about 1.4, at most about 1.5, at most about 1.6, at most about 1.7, at most about 1.8, at most about 1.9, at most about 2.0, at most about 2.5, at most about 3.0, at most about 4.0, at most about 5.0, at most about 6.0, or at most about 10.

In some embodiments, the use of the nucleocytoplasmic transport inhibitor increases the replication of the oncolytic virus (e.g., MYXV or VACV) in the cancer cell or cancer tissue. In some embodiments, the oncolytic virus is replicated at a rate that is at least 20%, 30%, 40%, 50%, 60%, 70%, 80%, 90% faster than the replication rate in the absence of the nucleocytoplasmic transport inhibitor. In some embodiments, the oncolytic virus is replicated at a rate that is at least 1.5 times, 2 times, 2.5 times, 3 times, 3.5 times, 4 times, 5 times, 6 times, 7 times, 8 times, 9 times, or 10 times faster than the replication rate in the absence of the nucleocytoplasmic transport inhibitor. In some embodiments, the nucleocytoplasmic transport inhibitor increases the replication of the oncolytic virus in the cancer cell or cancer tissue by at least 30%, 50%, 70%, 90%, 2 fold, 3 fold, 5 fold, 7 fold, 9 fold, 10 fold, 12 fold, or 15 fold after 24 hours post infection. In some embodiments, the nucleocytoplasmic transport inhibitor increases the replication of the oncolytic virus in the cancer cell or cancer tissue by no more than 5 fold, 10 fold, 12 fold, 15 fold, 20 fold, 30 fold, 50 fold, 70 fold, or 100 fold after 24 hours post infection.

In some embodiments, the use of the nucleocytoplasmic transport inhibitor in combination with an oncolytic virus reduces the viability of the cancer cell or cancer tissue compared to the use of the oncolytic virus in the absence of the nucleocytoplasmic transport inhibitor. In some embodiments, the cell viability is reduced for at least about 20%, at least about 30%, at least about 40%, at least about 50%, at least about 60%, at least about 70%, at least about 80%, or at least about 90% of cancer cells compared to the cell viability when using the oncolytic virus in the absence of the nucleocytoplasmic transport inhibitor.

Further disclosed is a delivery strategy where the therapeutic MYXV virus is first incubated with mixed leukocytes ex vivo from either bone marrow or peripheral blood mononuclear cells prior to introducing the cells into a subject with cancer. In some embodiments, the leukocytes and the MYXV are incubated together with a nucleocytoplasmic transport inhibitor ex vivo. In this strategy, MYXV may be delivered to cancer sites via migration of leukocytes pre-infected with virus ex vivo. This systemic delivery method is sometimes called "ex vivo virotherapy", or EVV (aka EV2), because the virus is first delivered to isolated leukocytes prior to infusion into the patient. The MYXV construct and this delivery strategy may significantly reduce tumor burden and increase survival in a subject in need thereof In some embodiments, the BM or PBMC cells are incubated with MYXV constructs for one hour ex vivo, and then the MYXV-loaded leukocytes are infused back into the recipient. In some embodiments, incubation with the nucleocytoplasmic transport inhibitor increases uptake of MYXV by the leukocytes and/or increases delivery of MYXV to the tumor sites.

In certain embodiments, the mononuclear peripheral blood cells and/or bone marrow cells are obtained from the subject, for example as autologous cells. In some embodiments, the mononuclear peripheral blood cells and/or bone marrow cells are obtained from one or more allogeneic donors, for example, a donor that is matched to the recipient for at least 1, at least 2, at least 3, at least 4, at least 5, at least 6, at least 7, or at least 8 HLA alleles (such as one or both copies of HLA-A, HLA-B, HLA-A, and/or HLA-DR alleles). HLA alleles can be typed, for example, using DNA-based methods. In some embodiments, the mononuclear peripheral blood cells and/or bone marrow cells are obtained from one or more heterologous donors.

Method of Increasing Virus Yield

Disclosed herein, in one aspect, is a method for replicating an oncolytic virus such as a poxvirus, comprising: exposing a host cell to an effective amount of a nucleocytoplasmic transport inhibitor and the oncolytic virus under conditions that permit the oncolytic virus to adsorb to the surface of the host cell, and incubating the infected host cell in a culture medium to allow for replication of the oncolytic virus. In some embodiments, the oncolytic virus is a poxvirus. In some embodiments, the oncolytic virus is MYXV.

In some embodiments, the method further comprising harvesting the poxvirus produced in the host cell. In some embodiments, the method further comprises contacting the host cell with the nucleocytoplasmic transport inhibitor prior to infecting the host cell with the poxvirus. In some embodiments, the method further comprises contacting the host cell with the nucleocytoplasmic transport inhibitor after infecting the host cell with the poxvirus. In some embodiments, the method further comprises exposing the host cell to the nucleocytoplasmic transport inhibitor and the poxvirus at the same time. In some embodiments, the poxvirus is replicated at a rate that is at least 30% faster than a replication rate in an absence of the nucleocytoplasmic transport inhibitor. In some embodiments, the nucleocytoplasmic transport inhibitor increases the replication of the poxvirus by at least 3 fold after 24 hours post infection. In some embodiments, the host cell is contacted with the poxvirus at a multiplicity of infection (MOI) lower than 2.0. In some embodiments, the effective amount of the nucleocytoplasmic transport inhibitor is in the range of about 0.0005 µM to about 0.5 µM. In some embodiments, the culture medium comprises the nucleocytoplasmic transport inhibitor. In some embodiments, the host cell is an immortalized human or primate cell. In some embodiments, the host cell is from a cell line used in good manufacturing practices (GMP) for manufacture of the poxvirus. In some embodiments, the host cell is a Human A549 cell, a HeLa cell, a 239 cell, or a primate Vero cell. In some embodiments, the method further comprises removing un-adsorbed poxvirus.

Disclosed herein, in some aspects, is a method of producing an oncolytic virus at an increased growth rate and/or titer in cells, the method comprising: contacting a host cell with an effective amount of a nucleocytoplasmic transport inhibitor; contacting the host cell with a oncolytic virus of interest under conditions that permit the oncolytic virus of interest to adsorb to a surface of the host cell; and culturing the host cell to produce progeny of the oncolytic virus of interest. In some embodiments, the method further comprises harvesting the progeny of the oncolytic virus of interest. In some embodiments, the oncolytic virus is a poxvirus. In some embodiments, the oncolytic virus is MYXV.

Disclosed herein, in some embodiments, are methods for increasing or enhancing oncolytic virus gene expression and progeny virus formation using drug inhibitors of the nucleocytoplasmic transport pathway. In some embodiments, inhibition of the nuclear export pathway in immortalized human cells commonly used for the GMP manufacture of oncolytic virus can be used to increase the viral yield from these cells. Thus, the disclosure provides a robust method of manufacturing potentially therapeutic oncolytic virus such as In some embodiments, the oncolytic virus is MYXV.

In some embodiments, this enhanced virus replication is most potent when cells are treated with an effective amount of inhibitor, for example, beginning just prior to the time of first virus adsorption. In some embodiments, an effective amount of inhibitor is determined for a given cell culture system (e.g., a given inhibitor, virus strain and host cell line). An effective amount of inhibitor can be determined, for example, by titrating the amount of the inhibitor in the cell culture system, and quantifying the yield of viral progeny as disclosed herein. In some embodiments, an effective amount of inhibitor can minimize drug-specific cellular toxicity, while increasing the yield of viral progeny. In some embodiments, an effective amount of a nucleocytoplasmic transport inhibitor is about 0.000001 µM to about 1 µM, about 0.000001 µM to about 0.1 µM, about 0.00001 µM to about 0.1 µM, about 0.00005 µM to about 0.05 µM, or about 0.00005 µM to about 0.005 µM. In some embodiments, an effective amount of a nucleocytoplasmic transport inhibitor is greater than about 0.000001 µM, about 0.000005 µM, about 0.00001 µM, about 0.00005 µM, about 0.0001, about 0.0005 µM, about 0.001 µM, about 0.005 µM, about 0.01 µM, about 0.05 µM, or about 0.1 µM. In some embodiments, an effective amount of a nucleocytoplasmic transport inhibitor is no more than about 0.0005 µM, about 0.001 µM, about 0.0015 µM, about 0.002 µM, about 0.0025 µM, about 0.003 µM, about 0.0035 µM, about 0.004 µM, about 0.0045 µM, about 0.005 µM, about 0.01 µM, about 0.015 µM, about 0.02 µM, about 0.025 µM, about 0.03 µM, about 0.035 µM, about 0.04 µM, about 0.045 µM, about 0.05 µM, about 0.1 µM, about 0.2 µM, about 0.25 µM, about 0.3 µM, about 0.4 µM, about 0.5 µM, about .75 µM, about 0.9 µM, about 1µM, about 1.25 µM, about 1.5 µM, about 1.75 µM, about 2 µM, about 3 µM, about 4 µM, about 5 µM, about 6 µM, about 7 µM, about 8 µM, about 9 µM, or about 10 µM.

In some embodiments, enhanced virus replication occurs when the cells are infected at an effective multiplicity of infection (MOI) and then, for example, maintained in the continuous presence of the nucleocytoplasmic transport inhibitor. The MOI can be determined for a given cell culture system (e.g., a given inhibitor, virus strain and host cell line), for example, by titrating the ratio or virus to host cells in the cell culture system, and quantifying the yield of viral progeny as disclosed herein. In some embodiments, an effective MOI can minimize drug-specific cellular toxicity, while enhancing replication of the virus and increasing the yield of viral progeny.

The host cells can be contacted with a poxvirus of interest (e.g., MYXV) under conditions that permit the poxvirus of interest to adsorb to the surface of the host cells. In certain embodiments, the cells are contacted with the poxvirus of interest at a multiplicity of infection (MOI) of between about 0.001 to 2.0 or about 0.01 and 1.0, such as about 0.001 MOI, about 0.005 MOI, 0.01 MOI, about 0.02 MOI, about 0.03 MOI, about 0.04 MOI, about 0.05 MOI, about 0.06 MOI, about 0.07 MOI, about 0.08 MOI, about 0.09 MOI, about 0.1 MOI, about 0.15 MOI, about 0.2 MOI, about 0.25 MOI, about 0.3 MOI, about 0.35 MOI, about 0.4 MOI, about 0.45 MOI, about 0.5 MOI, about 0.55 MOI, about 0.6 MOI, about 0.65 MOI, about 0.7 MOI, about 0.75 MOI, about 0.8 MOI, about 0.85 MOI, about 0.9 MOI, about 0.95 MOI, about 1.0 MOI, about 1.1 MOI, about 1.2 MOI, about 1.3 MOI, about 1.4 MOI, about 1.5 MOI, about 1.6 MOI, about 1.7 MOI, about 1.8 MOI, about 1.9 MOI, or about 2.0 MOI. In some embodiments, the un-adsorbed poxvirus of interest is removed prior to culturing cells, for example by washing the cells. After treatment with the nucleocytoplasmic transport inhibitor, the host cells are cultured in the presence of the drug to produce progeny of the poxvirus of interest. Appropriate culture conditions can be selected based on the specific cell type. In some embodiments, the cells are allowed to incubate with the poxvirus of interest for a period of time to allow the poxvirus of interest to adsorb to the surface of the host cells, such as about 20 minutes to about 5 hours, for example about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 2 hours, about 2.5 hours, about 3 hours, about 3.5 hours, about 4 hours, about 4.5 hours, about 5 hours, 12 hours, 18 hours, 20 hours, 24 hours, 30 hours, 36 hours, or even longer. In certain embodiments, the host cells are cultured in the presence of an effective amount of nucleocytoplasmic transport inhibitor, for example at the concentrations described above. The host cells can be cultured from about one to several days, such as 3 to 5 days before the progeny virus is harvested. In some embodiments, the method includes harvesting the progeny of the poxvirus of interest.

As disclosed herein, nucleocytoplasmic transport inhibitors can enhance virus replication and progeny virus yield in such cells. This drug-augmentation method provides a practical method to increase the yield of poxviruses, such as MYXV and VACV, which can be exploited for the large scale GMP production and clinical use of these viruses. In some embodiments, this disclosure demonstrates that nucleocytoplasmic transport inhibitors can be used to increase the yield of poxviruses, including oncolytic virus candidates such as vaccinia virus (VACV) and myxoma virus (MYXV), when applied to poxvirus GMP manufacture in immortalized human or primate cells.

The present disclosure provides a method of increasing poxvirus production yields in transformed human and primate cells, for example, those commonly used for GMP manufacture or viruses, such as oncolytic viruses. In comparison with other viruses that have been put forward as oncolytic virus candidates, poxviruses such as MYXV and VACV present some unique challenges in large-scale manufacture and purification. Due to its large size, vaccinia virus cannot be sterilized by filtration and thus any manufacturing process is typically closed. With its entire life cycle occurring within the host cell cytoplasm, the bulk of infectious particles are not released into the cellular medium, but are retained within the infected cell, thus purification requires the lysis of the infected cell and the purification of the viral particles from the cellular debris.

Disclosed herein, in some embodiments, are methods of treating immortalized human cell lines with agents, such as small molecules, that inhibit the nuclear export pathway, for example when added just before the time of virus adsorption. Culturing the cells in the presence of the agents, for example, throughout subsequent infection cycles, can increase the replication and ultimate yields of overall infectious poxvirus. The disclosed method thus provides an elegant way to increase the overall yield of poxviruses, such as myxoma virus (MYXV) and vaccinia virus (VACV), in transformed human and primate cells used for virus GMP manufacture.

The use of the nucleocytoplasmic transport inhibitor increases the replication of poxvirus. In some embodiments, the poxvirus is replicated at a rate that is at least 20%, 30%, 40%, 50%, 60%, 70%, 80%, 90% faster than the replication rate in the absence of the nucleocytoplasmic transport inhibitor. In some embodiments, the poxvirus is replicated at a rate that is at least 1.5 times, 2 times, 2.5 times, 3 times, 3.5 times, 4 times, 5 times, 6 times, 7 times, 8 times, 9 times, or 10 times faster than the replication rate in the absence of the nucleocytoplasmic transport inhibitor.

In some embodiments, the nucleocytoplasmic transport inhibitor increases the replication of poxvirus by at least 30%, 50%, 70%, 90%, 2 fold, 3 fold, 5 fold, 7 fold, 9 fold, 10 fold, 12 fold, or 15 fold after 24 hours post infection. In some embodiments, the nucleocytoplasmic transport inhibitor increases the replication of poxvirus by no more than 5 fold, 10 fold, 12 fold, 15 fold, 20 fold, 30 fold, 50 fold, 70 fold, or 100 fold after 24 hours post infection.

Aspects of the present disclosure concern a method of producing oncolytic viruses such as poxviruses at an increased growth rate and/or titer in cells. In some embodiments, the method includes contacting host cells with an effective amount of nucleocytoplasmic transport inhibitor (which may also be referred to as a nuclear export pathway inhibitor). The concentration of inhibitor can be chosen to be below that which would normally cause any cytotoxic or anti-viral effects, but still sufficient to result in an increase in the production of the poxvirus of interest. In some embodiments, an effective amount of a nucleocytoplasmic transport inhibitor is between about 0.000001 μM and about 0.1 μM, such as about between about 0.000001 μM, about 0.00001 μM, about 0.0001, about 0.0005 μM and about 0.05 μM, such as about 0.0005 μM, about 0.001 μM, about 0.0015 μM, about 0.002 μM, about 0.0025 μM, about 0.003 μM, about 0.0035 μM, about 0.004 μM, about 0.0045 μM, about 0.005 μM, about 0.01 μM, about 0.015 μM, about 0.02 μM, about 0.025 μM, about 0.03 μM, about 0.035 μM, about 0.04 μM, about 0.045 μM, and about 0.05 μM.

Pharmaceutical Composition

In one aspect, disclosed herein are pharmaceutical compositions comprising an oncolytic virus, a nucleocytoplasmic transport inhibitor, a pharmaceutically acceptable excipient or carrier, or a combination thereof. When administered as a combination, the therapeutic agents (i.e., the oncolytic virus and the nucleocytoplasmic transport inhibitor) can be formulated as separate compositions that are given at the same time or different times, or the therapeutic agents can be given as a single composition.

The compositions can be administered once daily, twice daily, once every two days, once every three days, once every four days, once every five days, once every six days, once every seven days, once every two weeks, once every three weeks, once every four weeks, once every two months, once every six months, or once per year. The dosing interval can be adjusted according to the needs of individual subject. In certain embodiments, the therapeutic agents of the disclosure are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the therapeutic agents to be administered for the remainder of the patient's life. In some embodiments, the patient is monitored to check the progression of the disease or disorder, and the dose is adjusted accordingly. In some embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

To prepare the pharmaceutical compositions according to the present disclosure, a therapeutically effective amount of one or more of the therapeutic agents can be intimately admixed with a pharmaceutically acceptable carrier according to conventional pharmaceutical compounding techniques to produce a dose. A carrier may take a wide variety of forms depending on the form of preparation desired for administration, e.g., ocular, oral, topical or parenteral, including gels, creams ointments, lotions and time released implantable preparations, among numerous others. In certain embodiments, the pharmaceutically acceptable carrier is an aqueous solvent, i.e., a solvent comprising water, optionally with additional co-solvents. Exemplary pharmaceutically acceptable carriers include water, buffer solutions in water (such as phosphate-buffered saline (PBS)), and sugar alcohols such as sorbitol. Compositions suitable for parenteral administration can be enclosed in ampoules, disposable syringes or multiple dose vials made of glass or plastic. In some embodiments, formulations suitable for parenteral administration comprise aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

In some embodiments, the nucleocytoplasmic transport inhibitor is administered as a pharmaceutically acceptable salt, complex, or prodrug. Pharmaceutically acceptable salts or complexes can refer to appropriate salts or complexes of the active compounds according to the present disclosure which retain the desired biological activity of the parent compound and exhibit limited toxicological effects to normal cells. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

In some embodiments, the pharmaceutical composition is in a unit dosage form. In some embodiments, the unit dosage form is suitable to be administered intratumorally or parenterally, e.g., intravenously. Unit dosage formulations can be those containing a daily dose or unit, daily sub-dose, a weekly dose or unit, or an appropriate fraction thereof, of the administered ingredient. In some embodiments, a unit dose comprises from about 0.1 mL to about 100 mL deliverable volume, and/or ranges therebetween. In some embodiments, a unit dose comprises from about 0.5 mL to about 5 mL, from about 0.75 mL to about 2.5 mL, from about 0.9 mL to about 1.1 mL deliverable volume. In some embodiments, a unit dose comprises about 0.5 mL, about 1 mL, about 1.5 mL, or about 2 mL deliverable volume. In some embodiments, a unit dose comprises from about $1\times10^3$ plaque-forming units (PFU) to about $1\times10^{10}$ PFU of the oncolytic virus per mL, and/or ranges therebetween. In some embodiments, a unit dose comprises from about $1\times10^4$ PFU to about $1\times10^9$ PFU or from about $1\times10^6$ PFU to about $1\times10^8$ PFU of the oncolytic virus per mL, and/or ranges therebetween. In some embodiments, a unit dose comprises from about $1\times10^5$ PFU to about $1\times10^{10}$ PFU, from about $1\times10^6$ PFU to about $1\times10^{10}$ PFU, from about $1\times10^5$ PFU to about $1\times10^{11}$ PFU, from about $1\times10^5$ PFU to about $1\times10^9$ PFU, from about $1\times10^6$ PFU to about $1\times10^9$ PFU, or from about $1\times10^7$ PFU to about $1\times10^8$ PFU of the oncolytic virus per mL, and/or ranges therebetween.

In some embodiments, a unit dose comprises from about 1 picograms to about 1000 micrograms of the oncolytic virus, and/or ranges therebetween. In some embodiments, a unit dose comprises from about 10 picograms to about 100 micrograms of the oncolytic virus, and/or ranges therebetween. In some embodiments, a unit dose comprises from about 10 picograms to about 100 micrograms of the oncolytic virus, and/or ranges therebetween. In some embodiments, a unit dose comprises from about 10 picograms to about 10 micrograms, from about 10 picograms to about 1 microgram, from about 10 picograms to about 100 micrograms, from about 100 picograms to about 100 micrograms, from about 1000 picograms to about 100 micrograms, from about 10000 picograms to about 100 micrograms, from about 100 picograms to about 10 micrograms, or from about 100 picograms to about 1 microgram of the oncolytic virus, and/or ranges therebetween. In some embodiments, a unit dose comprises about 1 picogram, about 10 picograms, about 100 picograms, about 1 nanogram, about 10 nanograms, about 100 nanograms, about 1 microgram, about 10 micrograms, about 100 micrograms, or about 1000 micrograms of the oncolytic virus. In some embodiments, a unit dose comprises from about 0.01 picograms to about 500 micrograms of the nucleocytoplasmic transport inhibitor, and/or ranges therebetween. In some embodiments, a unit dose comprises from about 0.05 picograms to about 50 micrograms of the nucleocytoplasmic transport inhibitor, and/or ranges therebetween. In some embodiments, a unit dose comprises the nucleocytoplasmic transport inhibitor in a range of from about 0.1 picogram, about 1 picogram, about 10 picogram, about 100 picogram, or about 1 nanogram to about 0.1 microgram, about 1 microgram, about 10 micrograms, or about 50 micrograms, and/or ranges therebetween. In some embodiments, a unit dose comprises from about 10 picograms to about 10 micrograms, from about 10 picograms to about 1 microgram, from about 100 picograms to about 50 micrograms, from about 1000 picograms to about 50 micrograms, from about 10000 picograms to about 50 micrograms, from about 100 picograms to about 5 micrograms, or from about 100 picograms to about 1 microgram of the nucleocytoplasmic transport inhibitor, and/or ranges therebetween. In some embodiments, a unit dose comprises about 0.05 picograms, about 0.5 picograms, about 5 picograms, about 50 picograms, about 500 picograms, about 5 nanograms, about 50 nanograms, about 500 nanograms, about 5 micrograms, about 50 micrograms, or about 500 micrograms of the oncolytic virus. In some embodiments, a unit dose comprises from about 0.05 picograms to about 50 micrograms of the nucleocytoplasmic transport inhibitor, and/or ranges therebetween. In some embodiments, a unit dose comprises from about 0.01 picograms to about 100 micrograms of the nucleocytoplasmic transport inhibitor, and/or ranges therebetween. In some embodiments, a unit dose comprises from about 0.05 picograms to about 100 micrograms of the nucleocytoplasmic transport inhibitor, and/or ranges therebetween. In some embodiments, a unit dose comprises from about 0.01 picograms to about 90 micrograms, from about 0.01 picograms to about 80 microgram, from about 0.01 picograms to about 60 micrograms, from about 0.01 picograms to about 50 micrograms, from about 0.05 picograms to about 80 micrograms, from about 0.05 picograms to about 40 micrograms, from about 0.1 picograms to about 50 micrograms, or from about 0.1 picograms to about 30 microgram of the nucleocytoplasmic transport inhibitor, and/or ranges therebetween. In some embodiments, a unit dose comprises about 0.01 picogram, about 0.05 picograms, about 0.075 picograms, about 0.1 picograms, about 0.5 picograms, about 1 picograms, about 5 picograms, about 10 picograms, about 100 picograms, about 500 picograms, about 1 nanogram, about 10 nanograms, about 100 nanograms, about 1 microgram, about 10 micrograms, or about 100 micrograms of the nucleocytoplasmic transport inhibitor. In some embodiments, a unit dose comprises from about 0.01 picograms to about 500 micrograms of the nucleocytoplasmic transport inhibitor, and/or ranges therebetween. In some embodiments, a unit dose comprises from about 0.05 picograms to about 50 micrograms of the nucleocytoplasmic transport inhibitor, and/or ranges therebetween. In some embodiments, a unit dose comprises the nucleocytoplasmic transport inhibitor in a range of from about 0.1 picogram, about 1 picogram, about 10 picogram, about 100 picogram, or about 1 nanogram to about 0.1 microgram, about 1 microgram, about 10 micrograms, or about 50 micrograms, and/or ranges therebetween. In some embodiments, a unit dose comprises from about 10 picograms to about 10 micrograms, from about 10 picograms to about 1 microgram, from about 100 picograms to about 50 micrograms, from about 1000 picograms to about 50 micrograms, from about 10000 picograms to about 50 micrograms, from about 100 picograms to about 5 micrograms, or from about 100 picograms to about 1 microgram of the nucleocytoplasmic transport inhibitor, and/or ranges therebetween. In some embodiments, a unit dose comprises about 0.05 picograms, about 0.5 picograms, about 5 picograms, about 50 picograms, about 500 picograms, about 5 nanograms, about 50 nanograms, about 500 nanograms, about 5 micrograms, about 50 micrograms, or about 500 micrograms of the nucleocytoplasmic transport inhibitor.

In some embodiments, a weight ratio of the oncolytic virus to the nucleocytoplasmic transport inhibitor is from about $1\times10^9$ to about $1\times10^{-9}$, and/or any ranges therebetween. In some embodiments, a weight ratio of the oncolytic virus to the nucleocytoplasmic transport inhibitor is from about $1\times10^8$ to about $1\times10^{-8}$, from about $1\times10^7$ to about $1\times10^{-7}$, from about $1\times10^6$ to about $1\times10^{-6}$, from about $1\times10^5$ to about $1\times10^{-5}$, from about $1\times10^4$ to about $1\times10^{-3}$, from about $1\times10^2$ to about $1\times10^{-2}$, or from about 10 to about 0.1. In some embodiments, a weight ratio of the oncolytic virus to the nucleocytoplasmic transport inhibitor is from about 1 to about $1\times10^{-9}$, from about 1 to about $1\times10^{-8}$, from about 1 to about $1\times10^{-7}$, from about 1 to about $1\times10^{-6}$, from about 1 to about $1\times10^{-5}$, from about 1 to about $1\times10^{-3}$, from about 1 to about $1\times10^{-2}$, or from about 1 to about 0.1. In some embodiments, a weight ratio of the oncolytic virus to the nucleocytoplasmic transport inhibitor is from about $1\times10^{-9}$ to about 1, from about $1\times10^{-8}$ to about 1, from about $1\times10^{-7}$ to about 1, from about $1\times10^{-6}$ to about 1, from about $1\times10^{-5}$ to about 1, from about $1\times10^{-4}$ to about 1, from about $1\times10^{-3}$ to about 1, from about $1\times10^{-2}$ to about 1, or from about 0.1 to about 1.

EXAMPLES

Example 1: Nucleocytoplasmic Transport Inhibitor Drugs Enhance MYXV Gene Expression in Non-Permissive Human Cancer Cell Lines In certain human cancer cell lines, MYXV gene expression is restricted, in particular late gene expression. Inhibition of MYXV gene expression can contribute to limiting viral replication. However, it is not clearly documented which pathways and cellular proteins restrict MYXV replication in these non-permissive human cancer cell lines. Nucleocytoplasmic transport inhibitors were tested in human cancer cell lines that generally restrict MYXV gene expression and replication, for example, colorectal adenocarcinoma cell line HT29, pancreatic cancer cell line PANC-1, and melanoma cell line MDA-MB-435.

Leptomycin B was tested as a representative nucleocytoplasmic transport inhibitor. Human HT29 (FIG. 1A and FIG. 1B), PANC-1 (FIG. 3A) and MDA-MB-435 (FIG. 4A) cells were mock treated or pre-treated with different concentrations of leptomycin B for 1 h. Cells were then infected with vMyx-GFP-TdTomato (a wild type MYXV expressing GFP under poxvirus synthetic early/late promoter and TdTomato under poxvirus p11 late promoter) at multiplicities of infection (MOI) of 5.0 or 0.5.

HT29 cells were pre-treated with different concentrations of Leptomycin B for 1 h and infected with vMyx-GFP-Tdtomato at an MOI of 0.5 or 5.0 in the presence of the inhibitor, and fluorescence images were taken at 24 h (FIG. 1A) or 48 h (FIG. 1B) post infection using a fluorescence microscope.

Figure 3A:
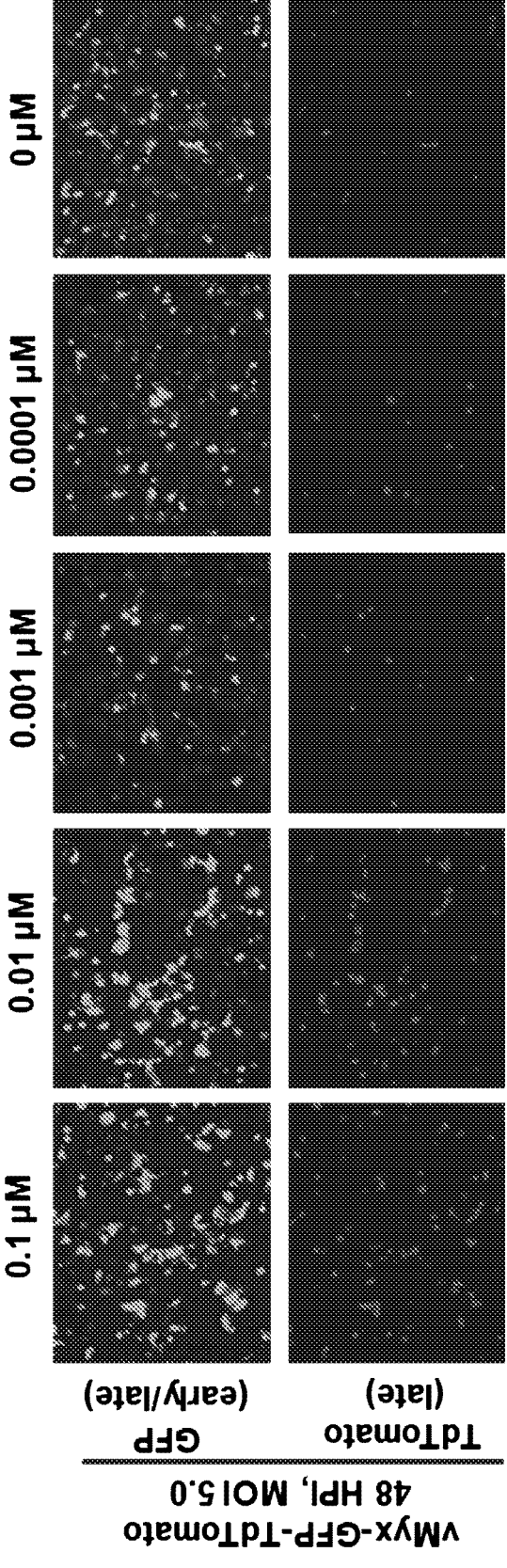
FIG. 3A and FIG. 3B illustrate the treatment of human pancreatic cancer cell line PANC-1 with nucleocytoplasmic transport inhibitor Leptomycin B enhanced MYXV gene expression and replication.

PANC-1 cells were pre-treated with different concentrations of Leptomycin B for 1 h and infected with vMyx-GFP-Tdtomato at an MOI of 5.0 in the presence of the inhibitor, and fluorescence images were taken at 48 h post infection using a fluorescence microscope (FIG. 3A).

Figure 4A:
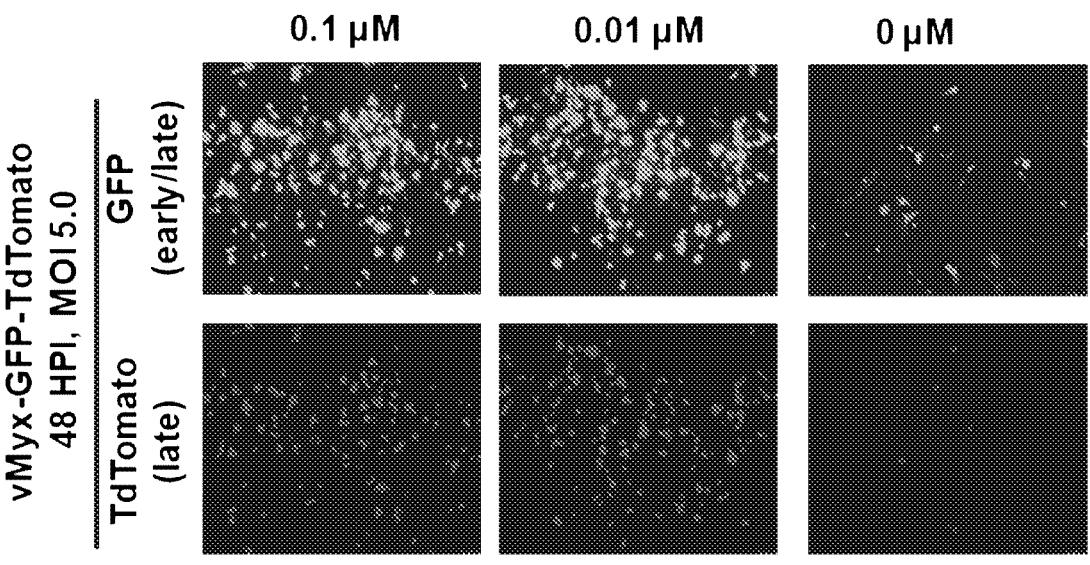
FIG. 4A and FIG. 4B illustrate the treatment of human melanoma cell line MDA-MB-435 with nucleocytoplasmic transport inhibitor Leptomycin B enhanced MYXV gene expression and replication.

MDA-MB-435 cells were pre-treated with different concentrations of Leptomycin B for 1 h and infected with vMyx-GFP-Tdtomato at an MOI of 5.0 in the presence of the inhibitor, and fluorescence images were taken at 48 h post infection using a fluorescence microscope (FIG. 4A).

The cells were observed under a fluorescence microscope to monitor expression of GFP and TdTomato, expression of which was indicative of the progression of virus infection. In the presence of leptomycin B (e.g., 1 µM, 0.1 µM and 0.01 µM), enhanced GFP (early/late) and TdTomato (late) expression were observed in all the tested human cancer cell lines (FIG. 1A, FIG. 1B, FIG. 3A, FIG. 4A). Treatment with nucleocytoplasmic transport inhibitor also allowed formation of small foci in these restricted human cancer cell lines.

These results show that treatment with a nucleocytoplasmic transport inhibitor enhances myxoma virus gene expression in infected cells. These results also suggest that certain nuclear proteins directly or indirectly restrict MYXV replication in these human cancer cell lines.

Example 2: Nucleocytoplasmic Transport Inhibitor Drug Treatment Enhances MYXV Progeny Virus Production in Non-Permissive Human Cancer Cell Lines To quantitatively assess whether the observed effect of nucleocytoplasmic transport inhibitor leptomycin B on viral gene expression can be reflected in progeny virus formation, quantitative virus titration assays were performed. HT29 (FIG. 2), PANC-1 (FIG. 3B) and MDA-MB-435 (FIG. 4B) human cancer cell lines were mock treated or pre-treated with different concentrations of leptomycin B.

HT29 cells were pre-treated with different concentrations of Leptomycin B for 1 h. The cells were then infected with vMyx-GFP-TdTomato at an MOI of 0.05 or 0.5 for 1 h. After 1 h the un-adsorbed viruses were removed, and then the cells were washed and incubated with media in the presence of the inhibitor. The infected cells were harvested at 72 h post infection, and virus titers were determined following serial dilutions onto RK13 cells. Leptomycin B treatment enhanced viral replication (FIG. 2).

PANC-1 cells were pre-treated with different concentrations of Leptomycin B for 1 h. The cells were then infected with vMyx-GFP-TdTomato at an MOI of 5.0 or 0.5 for 1 h. After 1 h the un-adsorbed viruses were removed, and then the cells were washed and incubated with media in the presence of the inhibitor. The infected cells were harvested at 48 h and 72 h post infection and virus titers were determined following serial dilutions onto RK13 cells. Leptomycin B treatment enhanced viral replication by at least 10-fold in all conditions (FIG. 3B).

MDA-MB-435 cells were pre-treated with different concentrations of Leptomycin B for 1 h, and then the cells were infected with vMyx-GFP-TdTomato at an MOI of 5.0 or 0.5 for 1 h. After 1 h the un-adsorbed viruses were removed, and then the cells were washed and incubated with media in the presence of the inhibitor. The infected cells were harvested at 48 h and 72 h post infection and virus titers were determined following serial dilutions onto RK13 cells. Leptomycin B treatment enhanced viral replication by at least 10-fold in all conditions (FIG. 4B).

Figure 2:
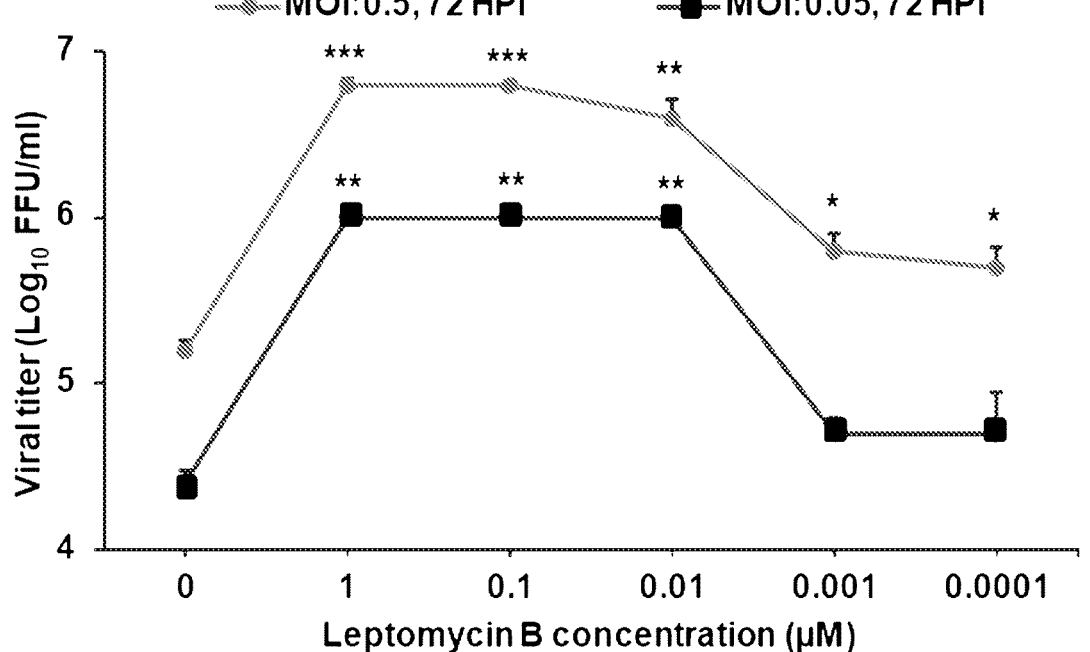
FIG. 2 illustrates that nucleocytoplasmic transport inhibitor Leptomycin B enhanced MYXV replication in human colorectal adenocarcinoma cell line HT29. HT29 cells were pre-treated with different concentration of Leptomycin B for 1 h. The cells were then infected with vMyx-GFP-TdTomato at an MOI of 0.5 or 0.05 for 1 h. After 1 h the un-adsorbed viruses were removed, the cells were washed and incubated with media in the presence of the inhibitor. The infected cells were harvested after 72 h post infection and virus titers were determined following serial dilutions onto RK13 cells.
Figure 3B:
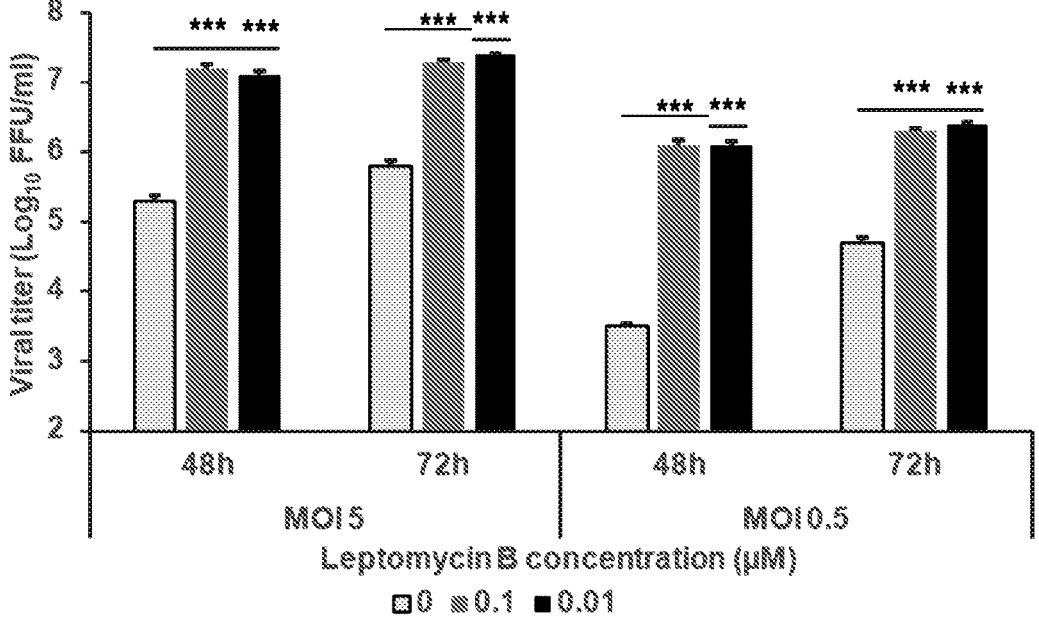
Figure 4B:
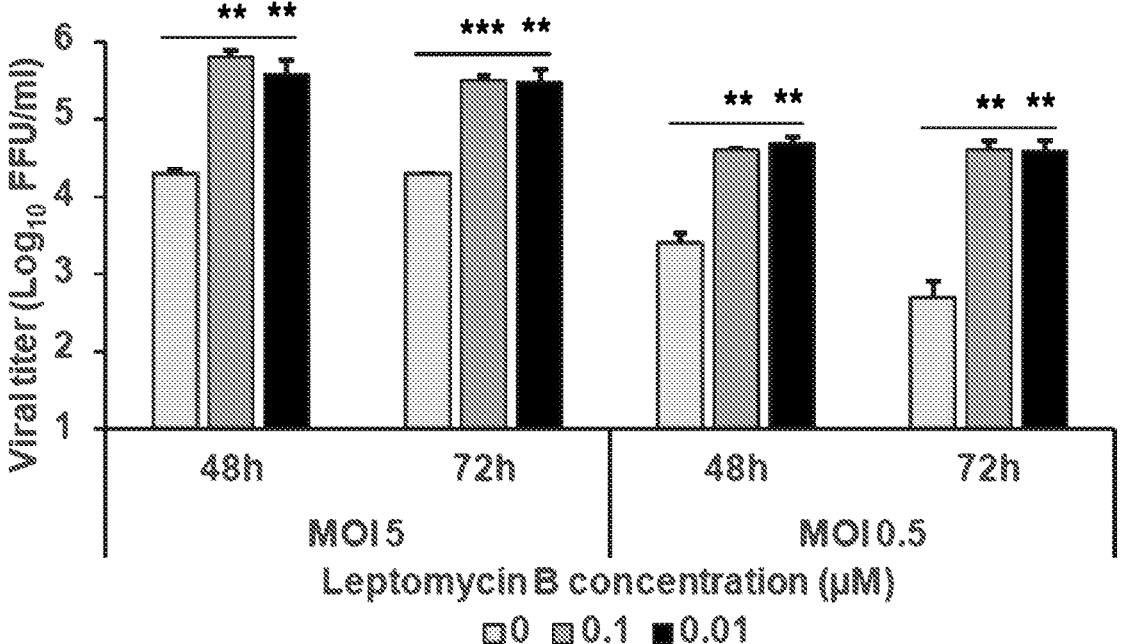

In all the tested cell lines Leptomycin B treatment significantly enhanced progeny MYXV formation at least 10 to 20 fold when infected with MOI 5.0 or 0.5 (FIG. 2, FIG. 3B, FIG. 4B). In contrast, in the permissive A549 cell line, Leptomycin B only increased viral replication at an MOI of 0.1 or lower.

These results indicated that blocking nuclear export pathways using the nucleocytoplasmic transport inhibitors can significantly enhance MYXV replication in non-permissive human cancer cell lines.

Example 3: Pretreatment of Human Cancer Cell Lines with Nucleocytoplasmic Transport Inhibitor Enhances MYXV-Mediated Cancer Cell Killing To test whether nucleocytoplasmic transport inhibitor-enhanced MYXV replication also enhanced cancer cell killing, viability of infected cells was tested by measuring the ATP. In this case HT29 and PANC-1 cells were tested.

Figure 5A:
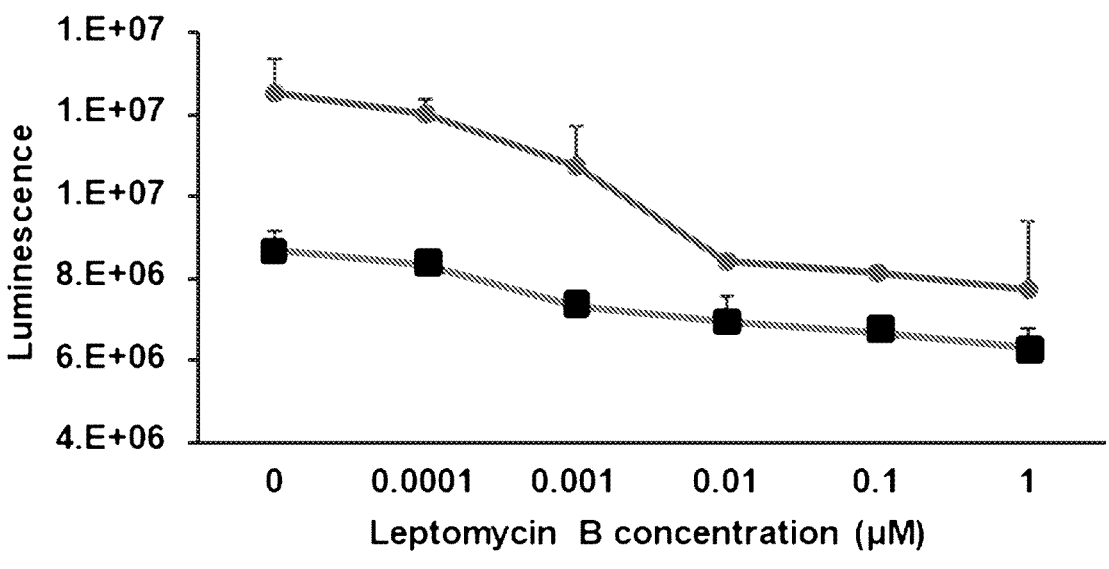
FIG. 5A and FIG. 5B illustrate the treatment of human cancer cell lines with nucleocytoplasmic transport inhibitor and subsequent infection with MYXV reduced cell viability.
Figure 5B:
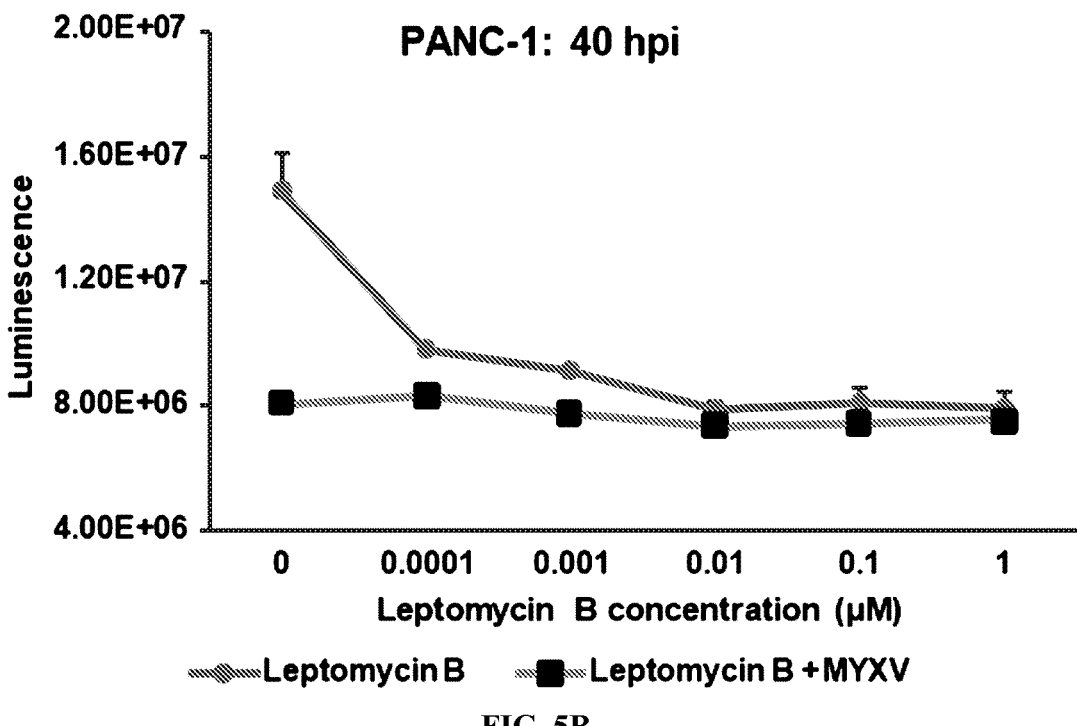

HT29 and PANC-1 cells were seeded in opaque-walled 96 well plates at 20,000 cells in 100 ul medium/well, and were cultured overnight. The cells were then treated with different concentrations of Leptomycin B for 1 h, and infected with vMyx-GFP at an MOI of 5.0 in the presence of the inhibitor. Cell viability was then measured based on ATP content. ATP content was measured at 64 h (HT-29 cells, FIG. 5A) or 40 h (PANC-1 cells, FIG. 5B) post infection by adding 100 ul CellTiter-Glo® reagent (Promega) and recording luminescence using a plate reader. Data shown represent the mean +/−SD (n=3 or 4).

The results showed that at the indicated time points, both HT29 and PANC-1 cells are sensitive to Leptomycin B treatment alone. With the increasing concentration of Leptomycin B the cell viability was decreased. At these time points (64 hpi for HT29 and 40 hpi for PANC-1) MYXV alone also reduced cell viability to 40-50%. However, pre-treatment of both HT29 and PANC-1 cells with Leptomycin B further reduced the viability of these human cancer cell lines. Interestingly, in HT29 cell line the lowest concentration of Leptomycin B that affected minimum cell viability, after combination with MYXV, further enhanced the cell killing ability of MYXV. Taken together these results showed that nucleocytoplasmic transport inhibitors not only can enhance MYXV replication in non-permissive human cancer cell lines but also synergistically enhance the cell killing ability of MYXV.

Example 4: Oncolytic Virotherapy with a Myxoma Virus (MYXV) and a Nucleocytoplasmic Transport Inhibitor A subject is identified as having a cancer (e.g., a non-permissive hematological cancer or solid tumor).

A MYXV is administered to the subject as disclosed herein (e.g., administered via injection or infusion), in combination with Selinexor, a nucleocytoplasmic transport inhibitor approved for use in human cancer patients. The MYXV infects cancer cells in the subject, leading to cancer cell death and an increased anti-tumor immune response. Administering the nucleocytoplasmic transport inhibitor enhances the anti-cancer activity of the myxoma virus, leading to a reduction in tumor burden and longer survival.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention.

Accordingly, this disclosure includes all modifications encompassed within the spirit and scope of the disclosure as defined by the following claims. We therefore claim as our invention all that comes within the scope and spirit of these claims.

We claim:

1. A method of enhancing susceptibility of a cancer cell to infection by an oncolytic virus, comprising contacting the cancer cell to an oncolytic virus and a nucleocytoplasmic transport inhibitor, wherein the nucleocytoplasmic transport inhibitor is Leptomycin B.

2. A pharmaceutical composition comprising:
   a. an oncolytic virus, and
   b. a nucleocytoplasmic transport inhibitor, wherein the nucleocytoplasmic transport inhibitor is Leptomycin B.

3. The pharmaceutical composition of claim 2, wherein the oncolytic virus is derived from the Poxviridae family.

4. The pharmaceutical composition of claim 2, wherein the oncolytic virus is derived from Chordopoxvirinae subfamily or Entomopoxvirinae subfamily.

5. The pharmaceutical composition of claim 2, wherein the oncolytic virus is derived from a virus genus of *Orthopoxvirus, Cervidpoxvirus, Parapoxvirus, Avipoxvirus, Capripoxvirus, Leporipoxvirus, Suipoxvirus, Molluscipoxvirus, Yatapoxvirus, Alphaentomopoxvirus, Betaentomopoxvirus,* or *Gammaentomopoxvirus.*

6. The pharmaceutical composition of claim 2, wherein the oncolytic virus is derived from genus *Leporipoxvirus.*

7. The pharmaceutical composition of claim 2, wherein the oncolytic virus is a myxoma virus (MYXV).

* * * * *